United States Patent
Tovey

(10) Patent No.: US 9,274,000 B2
(45) Date of Patent: Mar. 1, 2016

(54) TUNABLE LIGHT SOURCE SYSTEM WITH WAVELENGTH MEASUREMENT FOR A HYPER-SPECTRAL IMAGING SYSTEM

(71) Applicant: CORNING INCORPORATED, Corning, NY (US)

(72) Inventor: Cameron John Tovey, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/360,999

(22) PCT Filed: Nov. 29, 2012

(86) PCT No.: PCT/US2012/067040
§ 371 (c)(1),
(2) Date: May 28, 2014

(87) PCT Pub. No.: WO2013/082272
PCT Pub. Date: Jun. 6, 2013

(65) Prior Publication Data
US 2014/0327816 A1    Nov. 6, 2014

Related U.S. Application Data

(60) Provisional application No. 61/564,951, filed on Nov. 30, 2011.

(51) Int. Cl.
*G01J 3/28* (2006.01)
*G01J 9/00* (2006.01)
*G01J 3/433* (2006.01)
*G01N 21/77* (2006.01)
*H04N 5/235* (2006.01)
*G01J 3/12* (2006.01)

(52) U.S. Cl.
CPC ............. *G01J 3/28* (2013.01); *G01J 3/4338* (2013.01); *G01J 9/00* (2013.01); *G01N 21/7743* (2013.01); *H04N 5/2354* (2013.01); *G01J 2003/1243* (2013.01)

(58) Field of Classification Search
CPC ............. G01J 3/28; G01J 9/00; H04N 5/2354
See application file for complete search history.

(56) References Cited

U.S. PATENT DOCUMENTS

| | | |
|---|---|---|
| 4,815,843 A | 3/1989 | Tiefenthaler |
| 6,429,022 B1 | 8/2002 | Kunz |
| 6,690,690 B2 | 2/2004 | Marron ........................ 372/20 |
| 6,785,433 B2 | 8/2004 | Tiefenthaler |
| 6,882,433 B2 | 4/2005 | Marron et al. ............... 356/512 |
| 7,217,951 B2 | 5/2007 | Krishna |
| 7,310,153 B2 | 12/2007 | Kiesel |
| 7,355,162 B2 | 4/2008 | Sidorin |

(Continued)

FOREIGN PATENT DOCUMENTS

| | | |
|---|---|---|
| WO | 0116569 | 3/2001 |
| WO | 2004092730 | 10/2004 |

*Primary Examiner* — David Porta
*Assistant Examiner* — Faye Boosalis
(74) *Attorney, Agent, or Firm* — John L. Haack

(57) ABSTRACT

A tunable light source system with wavelength measurement capability for a hyper-spectral imaging system is disclosed. A method includes reference filtering a portion of a tunable light beam while tuning the center wavelength, detecting with at least one photodetector the reference-filtered tunable light beam and generating therefrom at least one detector signal that varies with the center wavelength, and determining a tunable center wavelength based on the at least one detector signal.

16 Claims, 16 Drawing Sheets

(56) References Cited

U.S. PATENT DOCUMENTS

| | | | |
|---|---|---|---|
| 7,497,992 B2 | 3/2009 | Cunningham | 422/82.05 |
| 7,519,096 B2 | 4/2009 | Bouma et al. | 372/102 |
| 7,559,055 B2 | 7/2009 | Yang et al. | 717/127 |
| 9,019,499 B2 | 4/2015 | Tovey | |
| 2006/0050271 A1 | 3/2006 | McDonald | |
| 2007/0020689 A1 | 1/2007 | Caracci | |
| 2008/0204760 A1 | 8/2008 | Gollier | |
| 2008/0315078 A1 | 12/2008 | Ono | |
| 2010/0296089 A1 | 11/2010 | Webb et al. | 356/326 |
| 2011/0109909 A1 | 5/2011 | Wu | 356/445 |

TUNABLE LIGHT SOURCE SYSTEM WITH WAVELENGTH MEASUREMENT FOR A HYPER-SPECTRAL IMAGING SYSTEM

CROSS-REFERENCE TO RELATED APPLICATIONS

This application claims the benefit of priority under 35 U.S.C. §371 of the International Application Ser. No. PCT/US12/67040 filed on Nov. 29, 2012, which claims the benefit of priority under 35 U.S.C.§119 of U.S. Provisional Application No. 61/564951 filed on Nov. 30, 2011, the content of which is relied upon and incorporated herein by reference in its entirety.

FIELD

The present disclosure relates to a tunable light source, and in particular to a tunable light source system for a hyper-spectral imaging system, where the tunable light source can measure the wavelength of its tunable light beam during the operation of the hyper-spectral imaging system.

BACKGROUND

Hyper-spectral imaging systems capture images for different electromagnetic spectra. An example hyper-spectral imaging system is a label-independent detection (LID) optical reader. A LID optical reader is used to detect drug binding to a target molecule such as a protein, or changes in living cells as cellular material is displaced in response to a drug. Certain types of LID optical readers measure changes in the refractive index on the surface of a resonant waveguide grating (RWG) biosensor of an array of RWG biosensors. The individual RWG biosensors are located in respective wells of a microplate.

In one type of LID optical reader, the different spectra for the hyper-spectral imaging process are provided by a light source that has a tunable wavelength. The tunable light source sweeps narrowband light over a range of center wavelengths. A digital camera captures the images of the RWG biosensors for the different center wavelengths. The wavelength bandwidth of the narrowband light is typically on the order of 1 nm to 2 nm.

To ensure an accurate RWG biosensor measurement, the center wavelength of the narrowband light must be known to a high degree of resolution. To date, achieving such high resolution has proven to be very expensive. Less costly methods for measuring and maintaining the center wavelength at an accurate value can make LID readers and other hyper-spectral imaging systems commercially more attractive.

SUMMARY

An aspect of the disclosure is a tunable light source system that includes a tunable light source that emits a tunable light beam having a tunable center wavelength $\lambda_C$. A light-deflecting element is disposed in the tunable light beam to deflect at least a portion of the tunable light beam. A reference filter having a reference bandwidth is disposed to filter the deflected portion of the tunable light beam to form a filtered light beam. At least one photodetector is arranged to detect the filtered light beam and generate at least one detector electrical signal representative of a detected light spectrum. A controller is operably connected to the tunable light source and the photodetector and is configured to receive the at least one detector electrical signal and determine therefrom the tunable center wavelength of the tunable light beam.

Another aspect of the disclosure is a method of measuring a center wavelength $\lambda_C$ of a tunable light beam from a tunable light source. The method includes reference filtering a portion of a tunable light beam while tuning the center wavelength $\lambda_C$. The method also includes detecting with at least one photodetector the reference-filtered tunable light beam and generating therefrom at least one detector signal $SD(\lambda_C)$ that varies with the center wavelength $\lambda_C$. The method also includes determining the center wavelength $\lambda_C$ based on the at least one detector signal $SD(\lambda_C)$.

Another aspect of the disclosure is a tunable light source system that emits a tunable light beam and measures a center wavelength $\lambda_C$ of the tunable light beam. The system has a light-deflecting element disposed to deflect at least a portion of the wavelength-tunable light beam. A reference filter having a reference bandwidth filters the deflected portion of the tunable light beam to form a filtered light beam. At least one photodetector detects the filtered light beam and generates at least one detector electrical signal representative of a detected light spectrum. A controller is operably connected to the tunable light source and the at least one photodetector and is configured to receive the at least one detector electrical signal and determine therefrom the center wavelength of the tunable light beam.

These and other aspects of the disclosure will be further understood and appreciated by those skilled in the art by reference to the following written specification, claims, and appended drawings.

BRIEF DESCRIPTION OF THE DRAWINGS

A more complete understanding of the present disclosure can be had by reference to the following detailed description when taken in conjunction with the accompanying drawings, where.

DETAILED DESCRIPTION

Reference is now made to embodiments of the disclosure, exemplary embodiments of which are illustrated in the accompanying drawings.

Figure 1:
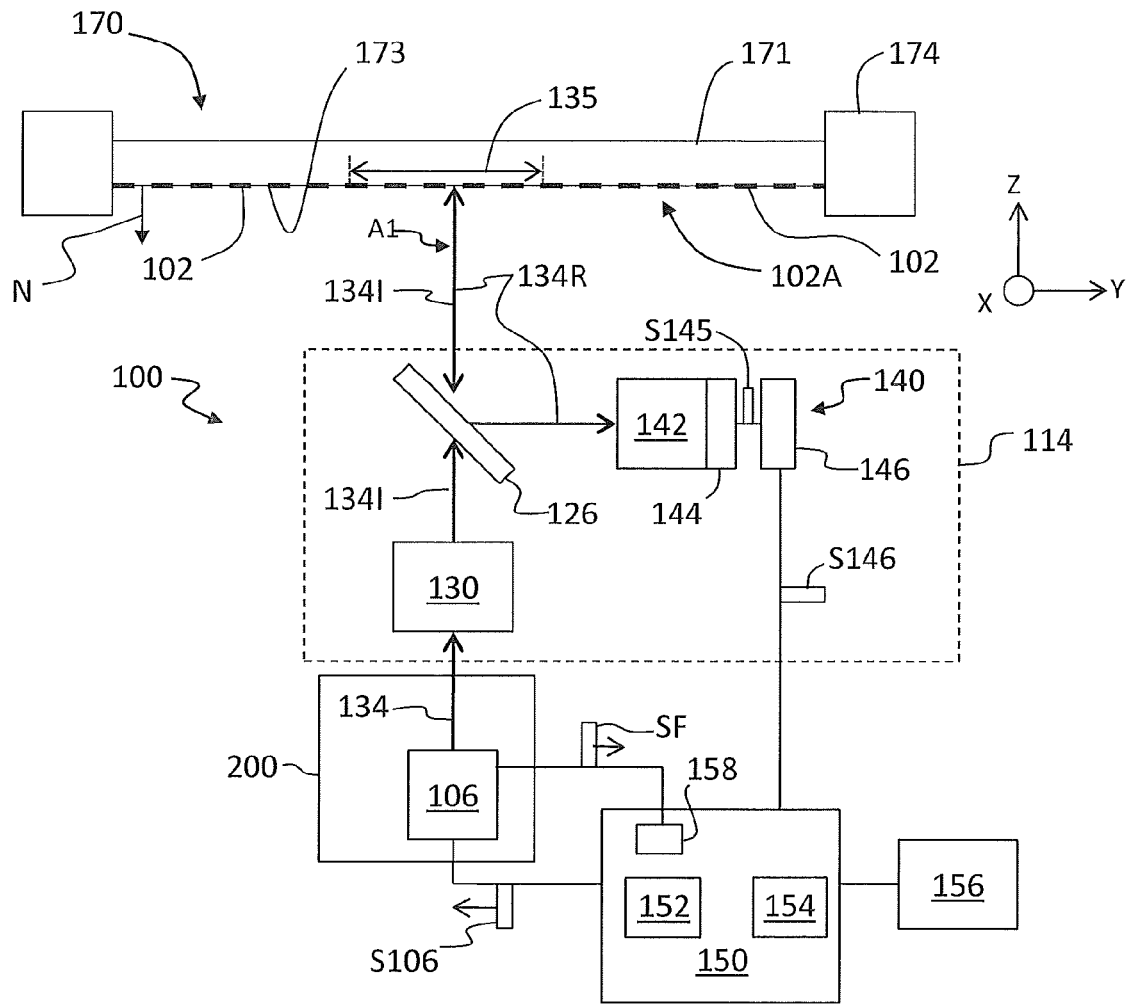
FIG. 1 is a generalized schematic diagram of an example optical reader system that includes the tunable light source system of the disclosure.

FIG. 1 is a generalized schematic diagram of an example optical reader system ("system") 100 suitable for use with the tunable light source systems and methods disclosed herein and described in greater detail below. The system 100 includes an imaging system 114 that is used to interrogate one or more resonant waveguide grating (RWG) biosensors 102. The imaging system 114 includes an illumination optical system 130 and an optical imager 140. Example imaging systems 114 are discussed in greater detail below. Example optical reader systems 100 with tunable light sources are disclosed in U.S. Pat. No. 7,599,055 and U.S. Patent Application Publications No. US2011/0109909 and US2010/0296089.

Figure 2:
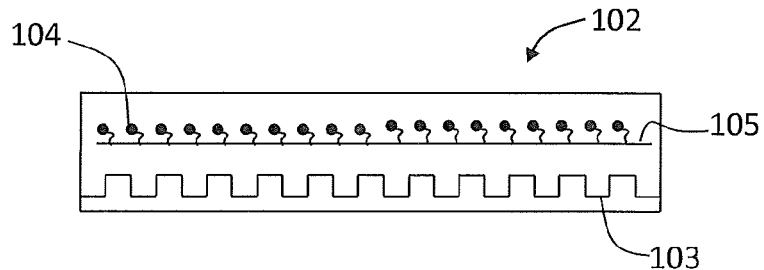
FIG. 2 is a close-up schematic view of an example RWG biosensor.
Figure 3:
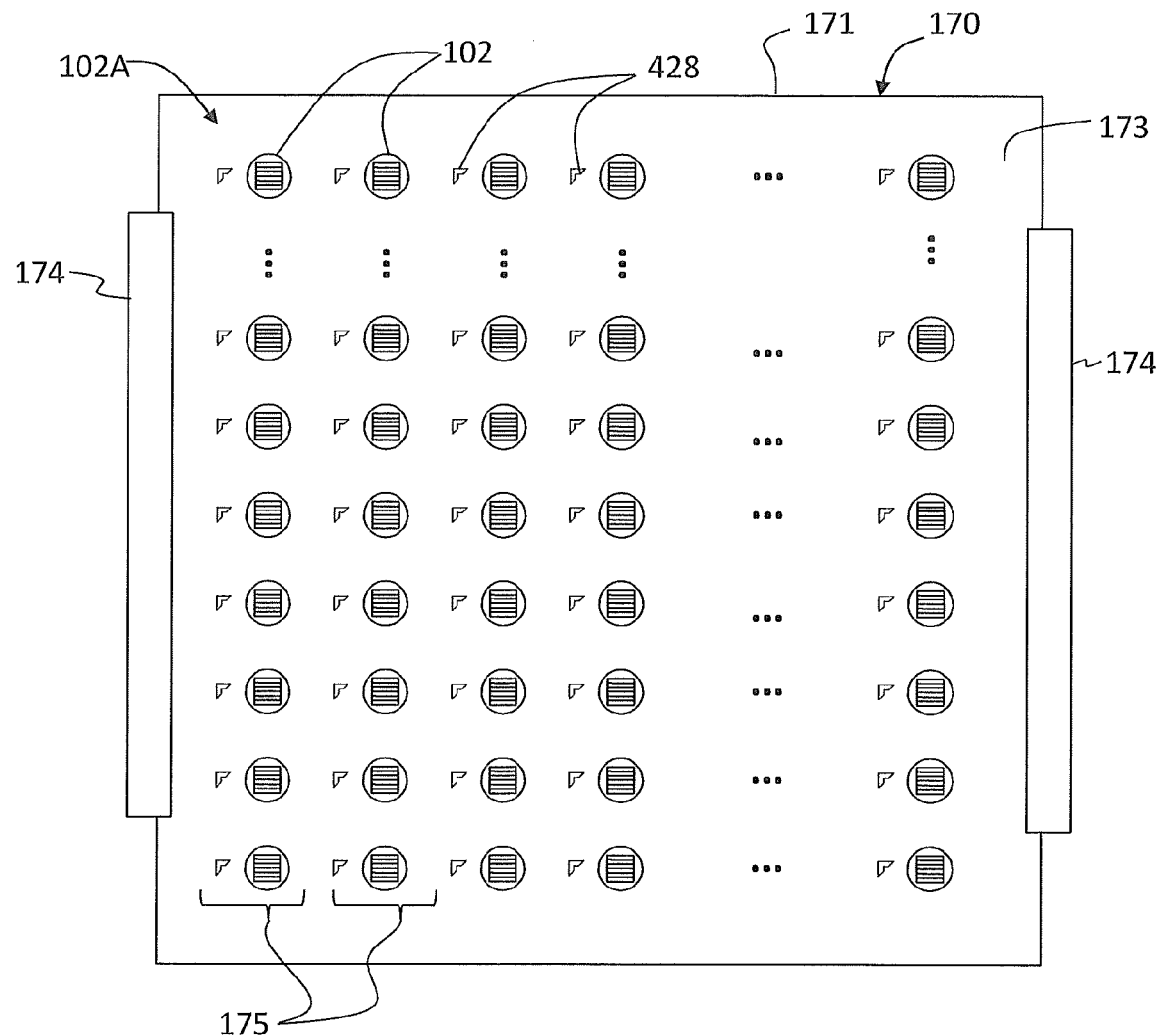
FIG. 3 is a face-on view of an example microplate that operably supports an array of RWG biosensors in associated regions or "wells," with the microplate being held by a microplate holder.
Figure 4:
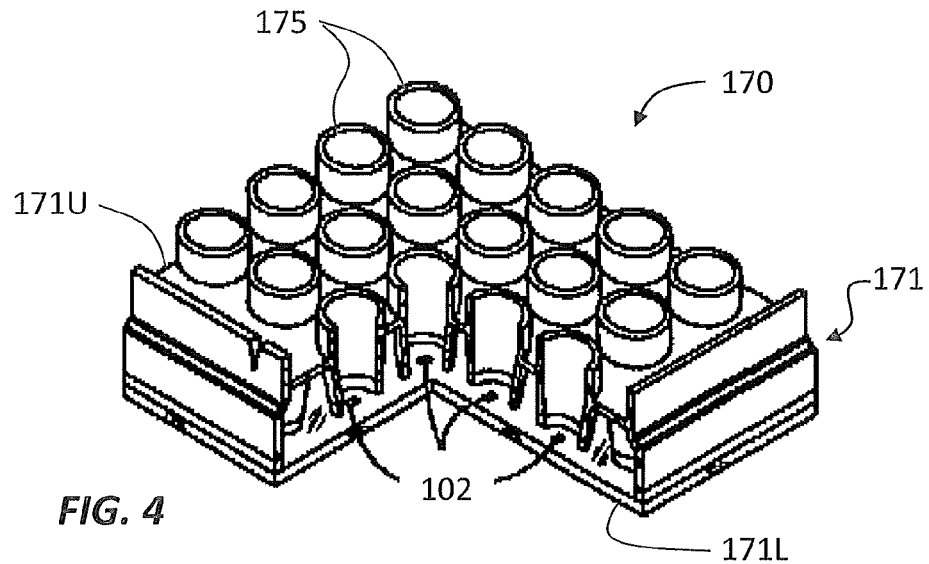
FIG. 4 is a cut-away perspective view of a portion of an example microplate.

FIG. 2 is a close-up schematic side view of an exemplary RWG biosensor 102, which has a grating 103 and a surface 105 configured so that a select bio-substance 104 (e.g., a biochemical material or a biochemical material such as cells, molecules, proteins, drugs, chemical compounds, nucleic acids, peptides, carbohydrates, etc.) affixes thereto. The RWG biosensors 102 need to be supported so that they can be optically interrogated. The typical support structure is called a "microplate." FIG. 3 is a face-on view of an example microplate 170 that comprises a support plate 171 with a surface 173 having a plurality of wells 175 formed therein. An example support plate 171 has a two-part construction of an upper plate 171U and a lower plate 171L, as shown in the partial view of FIG. 4 and as described, for example, in U.S. Patent Application Publication No. system 2007/0211245. Microplate surface 173 has a surface normal N (see FIG. 1).

The microplate 170 of FIG. 3 illustrates an exemplary configuration where RWG biosensors 102 are arranged in an array 102A and operably supported in wells 175. An exemplary RWG biosensor array 102A has a 4.5 mm pitch for RWG biosensors 102 that are 2 mm square, and includes 16 RWG biosensors per column and 24 RWG biosensors per row. In embodiments, fiducials 428 are used to position and/or align microplate 170 in system 100. A microplate holder 174 is also shown holding microplate 170. Many different types of plate holders can be used as microplate holder 174.

With reference again to FIG. 1, system 100 includes a tunable light source system 200, which is described in greater detail below. The tunable light source system 200 includes a tunable light source 106. The tunable light source 106 is configured to generate a narrow-wavelength tunable light beam 134 having a spectrum $L(\lambda, \lambda_C)$ and a spectral linewidth $\Delta\lambda_T$. The tunable light beam 134 is provided with a predetermined sequence of distinct center wavelengths $\lambda_C$ over a predetermined time period.

In embodiments, tunable light source 106 is configured to emit a time-series of narrow-band tunable light beams 134 having respective center wavelengths $\lambda_C$ ranging from 818 nm to 853 nm at a tuning speed of between 0.1 nm/sec and 300 nm/sec. The time-series of narrow-band tunable light beams ("tunable light beams") 134 can also be thought of as a single narrow-band light beam whose center wavelength $\lambda_C$ varies with time. Thus, in the discussion herein, tunable light beam 134 is also referred to in the singular.

Although tunable light source 106 is shown emitting tunable light beam 134 into free space, guided-wave configurations that use optical waveguides (e.g., optical fibers) can also be selected.

The tunable light beam 134 from tunable light source 106 passes to imaging system 114 and to illumination optical system 130, which has an associated optical axis A1. The illumination optical system 130 transforms tunable light beam 134 into at least one incident optical beam 134I. The incident optical beam 134I passes through a light-deflecting element 126 (e.g., a beam splitter) and is incident over an area 135 of microplate 170, wherein area 135 includes one or more RWG biosensors 102 (e.g., over 4×3 wells of a 384 well-formal microplate 170, over just one RWG biosensor, or over all of the RWG biosensors). In one example, incident optical beam 134I is moved (scanned) over RWG biosensor 102 to cover different areas 135 by either moving (scanning) illumination optical system 130 or by moving microplate 170 via microplate holder 174.

The incident optical beam 134I reflects from the one or more RWG biosensors 102, thereby forming a reflected optical beam 134R (i.e., reflected light). The reflected optical beam 134R is directed by light-deflecting element 126 to optical imager 140 having an imaging lens 142 and an image sensor 144 that captures an electronic (i.e., digital) image 145 (see FIG. 5) of the illuminated area 135 that includes the one or more RWG biosensors 102. The image sensor 144 generates a raw electronic image signal S145 representative of the captured electronic image 145. The optical imager 140 also includes image-sensor electronics 146 that pre-processes raw electronic image signals S145 from image sensor 144 and generates a pre-processed electrical image signal S146 representative of the pre-processed digital image. An example image sensor 144 is a charge-coupled device (CCD) chip such as the KAI-0340 CCD chip with a pixel size of 7.4 microns, available from Kodak, Inc., Rochester, N.Y., or a complementary metal oxide semiconductor (CMOS) chip. An example optical imager 140 is a CCD camera such as the Prosilica GE680 GigE camera, available from Prosilica, Burnaby, British Columbia, Canada, which camera has a maximum frame rate of 215 fps at VGA resolution. In embodiments, image sensor 144 can be an array of one or more photodiodes.

The system 100 also includes a controller 150 having a processor unit ("processor") 152 and a memory unit ("memory") 154. Example processors 152 include a computer, microprocessor, one or more central-processing units (CPU), a field-programmable gate array (FPGA) or the like. The memory 154 can be any type of digital memory used in computers, such as solid-state memory, magnetic memory and optical memory. The controller 150 receives pre-processed electrical image signal S146 from image-sensor electronics 146 and stores it in memory 154. The processor 152 analyzes digital images 145 embodied in pre-processed electrical image signals S146 based on instructions (e.g., image-processing software) stored therein or in memory 154. This process is discussed in greater detail below.

In embodiments, controller 150 includes or is operably connected to a display unit 156 that displays measurement information such as spectra plots, resonant wavelength plots and other measurement results, as well as system status and performance parameters. In embodiments, the spectra can be processed directly so that only the resonant wavelengths (as calculated, for example, as the respective centroids of measured spectra) are stored in memory 154.

In an example, controller 150 also includes a data acquisition card 158 that is electrically connected to tunable light source 106 and that receives a feedback signal SF from the tunable light source that includes information about a wavelength tuning parameter x, as discussed in greater detail below.

Example RWG biosensors 102 make use of changes in the refractive index at sensor surface 105 that affect the waveguide coupling properties of incident optical beam 134I and reflected optical beam 134R to enable label-free detection of bio-substance substance 104 on the RWG biosensor. The bio-substance 104 may be located within a bulk fluid deposited on RWG biosensor surface 105, and the attachment of this biochemical substance to the biosensor surface alters the index of refraction at the RWG biosensor 102.

To detect bio-substance 104, RWG biosensor 102 is probed with incident optical beam 134I, and reflected optical beam 134R is received at optical imager 140. The optical imager 140 is synchronized with tunable light source 106 so that as the center wavelength $\lambda_C$ of incident optical beam 134I is swept (tuned) over the wavelength band, the optical imager captures a series of digital images 145 corresponding to the different wavelengths. Thus, optical imager 140 obtains a sequence or series ("collection") 147 of RWG biosensor images 145, each of which corresponds to an incident optical beam 134I with a distinct center wavelength $\lambda_C$.

Figure 5:
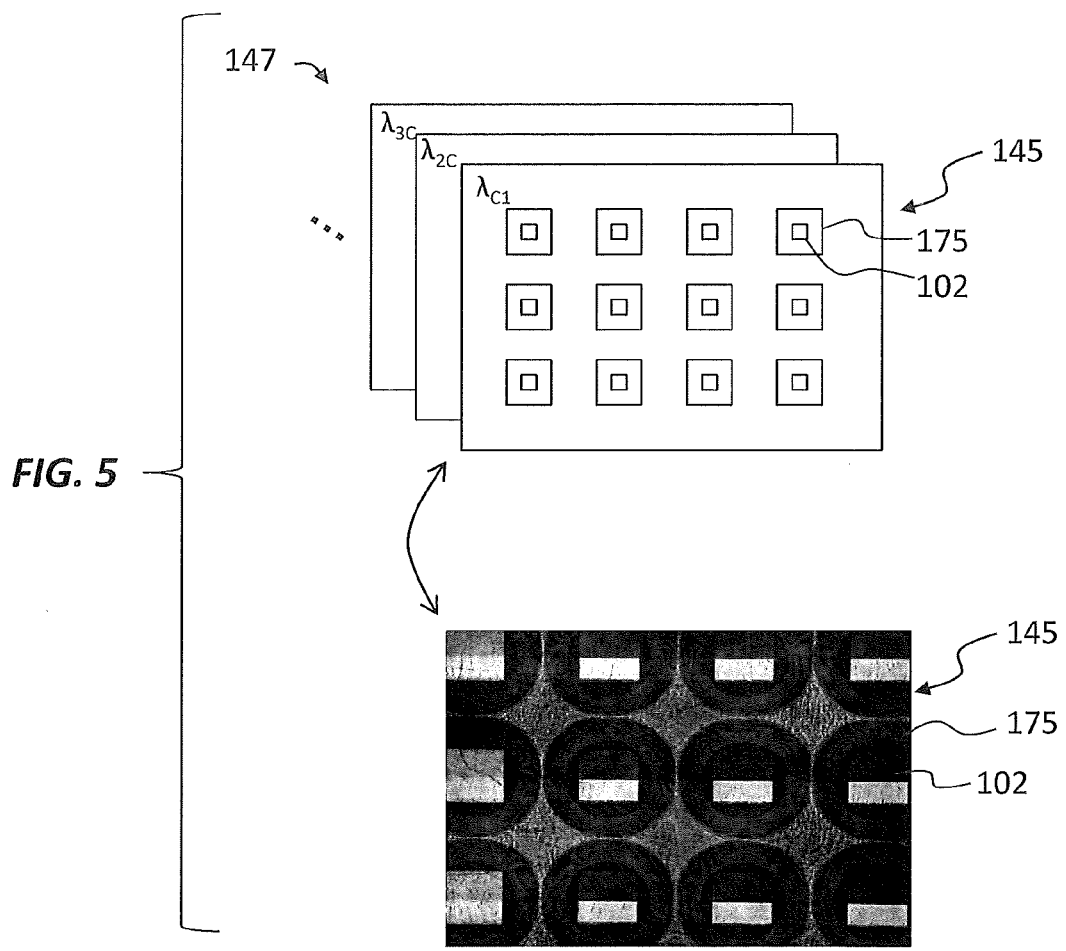
FIG. 5 is a schematic diagram illustrating a collection of digital images associated with different wavelengths of incident illumination provided by the tunable light source system.

FIG. 5 schematically illustrates the collection 147 of images 145 for different (central) wavelengths $\lambda_{C1}, \lambda_{C2}, \ldots \lambda_{Cj} \ldots \lambda_{Cn}$, which collection constitutes a "three-dimensional" (3D) data file or "data cube" of images. FIG. 5 also includes an example of an actual image 145. The optical imager 140 takes a sequence or series of images or pictures 145 of RWG biosensor(s) 102, where each image corresponds to one of the distinct center wavelengths $\lambda_{Cj}$ of the series of tunable light beams 134 emitted from tunable light source 106. Lastly, processor 152 receives and processes image collection 147 to determine, for example, whether there was a biochemical interaction or other event on one or more of RWG biosensors 102.

Figure 6:
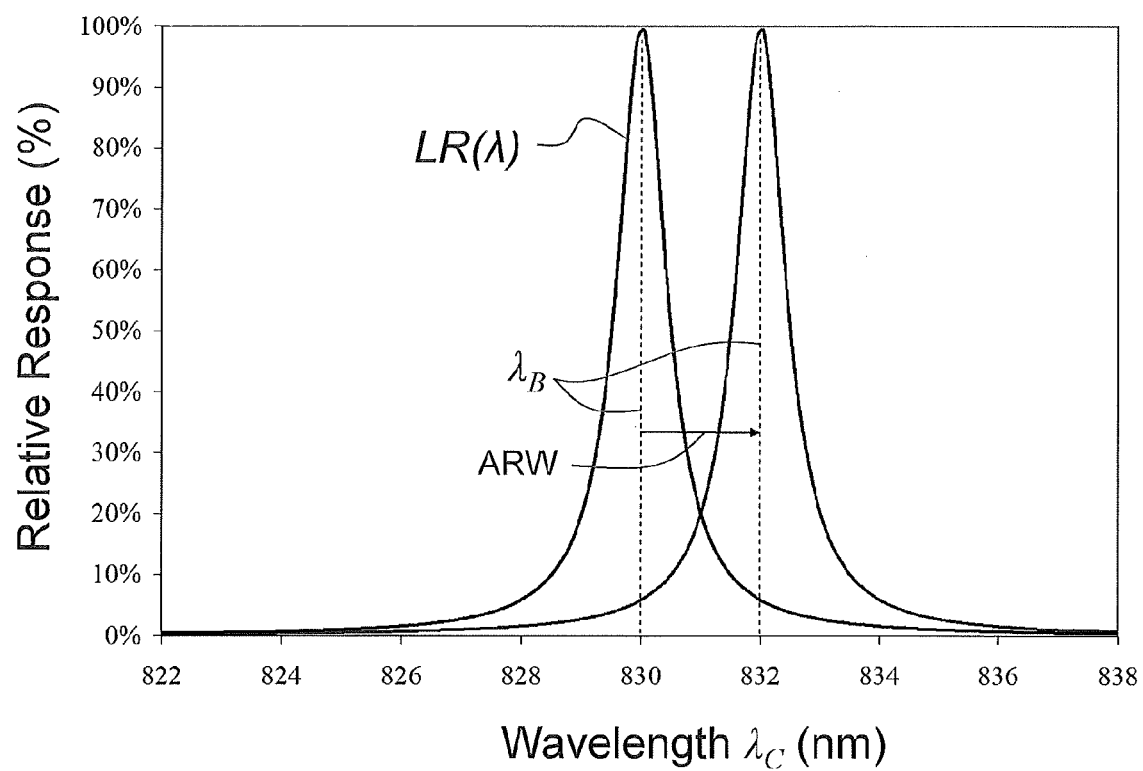
FIG. 6 plots the relative response (%) vs. the tuning wavelength $\lambda_C$ (nm) and shows an example RWG biosensor spectrum $LR(\lambda)$ as observed in one pixel of the image sensor as the center wavelength $\lambda_C$ is tuned, as well as the spectral shift (e.g. due to biological activity) in a later observation.

FIG. 6 plots the relative response (%) vs. the wavelength λ (nm) and shows an example first RWG biosensor spectrum LR(λ) with resonant wavelength $\lambda_B$ as observed in one pixel of image sensor 144 as the wavelength location $\lambda_C$ of light beam 134 is tuned from 822 to 838 nm. FIG. 6 also shows a second RWG biosensor spectrum observed in the same bio-substance 104 at a later time, with a shift in the resonant wavelength $\lambda_B$, e.g., as a result of changes in bio-substance 104 at the surface 105 of biosensor 106. The shift in the resonant wavelength is indicated by arrow ARW. In examples, system 100 needs to measure wavelength shifts $\delta\lambda_B$ in the peak (i.e., resonant wavelength $\lambda_B$) of the RWG biosensor spectrum LR(λ) with a repeatability of 1 picometer (pm).

In an example, tunable light beam 134 has spectrum L(λ, $\lambda_C$) is similar to the RWG biosensor reflected spectrum LR(λ) shown in FIG. 6. An example tunable light beam spectrum L(λ, $\lambda_C$) has a substantially Lorentzian or Gaussian distribution with a full width half maximum (FWHM) spectral width $\Delta L_T$ in the range of 1 nm to 2 nm. In an example, the center wavelength $\lambda_C$ of each spectrum L(λ, $\lambda_C$) ranges from 820 nm to 844 nm in 240 steps of 100 pm, and system 100 requires a wavelength repeatability of $1/100^{th}$ of an imaging frame to achieve the aforementioned 1 pm repeatability. In another example, the wavelength repeatability is not quite repeatable but controller 150 has knowledge of the center wavelength $\lambda_C$ for each biosensor measurement, i.e., for each frame to $1/100^{th}$ of an imaging frame. In another example, system 100 achieves a wavelength repeatability of $1/100^{th}$ of an imaging frame through precise knowledge of the center wavelength $\lambda_C$ and a suitable feedback mechanism.

The controller 150 is configured (e.g., processor 152 is programmed or operates under the control of software stored in memory 154) to detect changes (e.g., on the order of 1 part per million) in the RWG biosensor 102 refractive index caused by the presence of bio-substance 104. In embodiments, RWG biosensor surface 105 can be coated with, for example, biochemical compounds (not shown), or like biologically or chemically active materials, that allow surface attachment only of specific complementary bio-substance 104 such as antibodies or proteins, thereby enabling RWG biosensor 102 to be both highly sensitive and highly specific. In this way, system 100 and RWG biosensor 102 can be used to detect a variety of bio-substances 104. Likewise, RWG biosensor 102 can be used to detect the movements or changes in cells immobilized to RWG biosensor surface 105; for example, when the cells move relative to the RWG biosensor or when they incorporate or eject material, a refractive index change occurs.

If multiple RWG biosensors 102 are operably supported in array 102A in wells 175 of microplate 170, which in turn is supported by microplate holder 174, then they can be used to enable high-throughput drug or chemical screening studies. For a more detailed discussion about the detection of bio-substance 104 (or a biomolecular binding event) using scanning optical reader systems 100, see U.S. patent application Ser. No. 11/027,547. Other optical reader systems 100 are described in U.S. Pat. Nos. 7,424,187, 7,599,055, and 7,576,333, and U.S. Patent Application Publications No. system 2006/0205058 and system 2007/0202543.

The controller 150 and memory 154 therein receive collected pre-processed images 145 via pre-processed electronic image signals S146 for each center wavelength $\lambda_C$ in incident optical beam 134I, with image collection 147 forming the aforementioned "data cube" shown in FIG. 5. The processor 152 then uses image processing software to automatically process the image collection 147 to, for example: 1) determine whether there was a biochemical interaction or other event on one or more of the illuminated RWG biosensor(s) 102; 2) locate sensor region(s) or reference region(s), or both, on each of the illuminated RWG biosensor(s) 102; 3) remove defect regions on each of the illuminated RWG biosensor(s) 102; 4) calibrate a uniformity of surface chemistry and target molecule immobilizations on each of the illuminated RWG biosensor(s) 102; or a combination thereof.

If desired, processor 152 can bin together multiple imaging regions (pixels) with prior knowledge about the locations of sensor and reference regions (not shown) on RWG biosensors 102. In this mode, multiple pixels are grouped together as a single detector and the number of sensor spectra/images can be reduced to the number of binned regions. In this way, the data processing can be greatly simplified.

To achieve a data rate of 1 Hz for a specific interrogation application, the sequential scanning of tunable light source 106 and the sequential acquisition of spectral images 145 captured by optical imager 140 needs to be completed in 1 second. This requirement is well within the current capability of tunable light source 106 and tunable light source system 200. Of course, to meet this capability or any other data rate, the number of desired wavelength sampling points dictates the frame rate of image sensor 144 (and associated image-sensor electronics 146). For example, to obtain 500 wavelength samples during a single tuning sequence, the frame rate needs to be as fast as 500 frames per second (fps). The optical imager 140 in the form of a CMOS camera, such as the Basler A504k, is able to deliver 500 fps at a full 1024×1280 pixel format, with a higher frame rate being possible for partial-area images. In an application where it is not necessary to achieve a 1 Hz data rate, a slower optical imager 140 can be used.

Example Imaging Systems

Figure 7A:
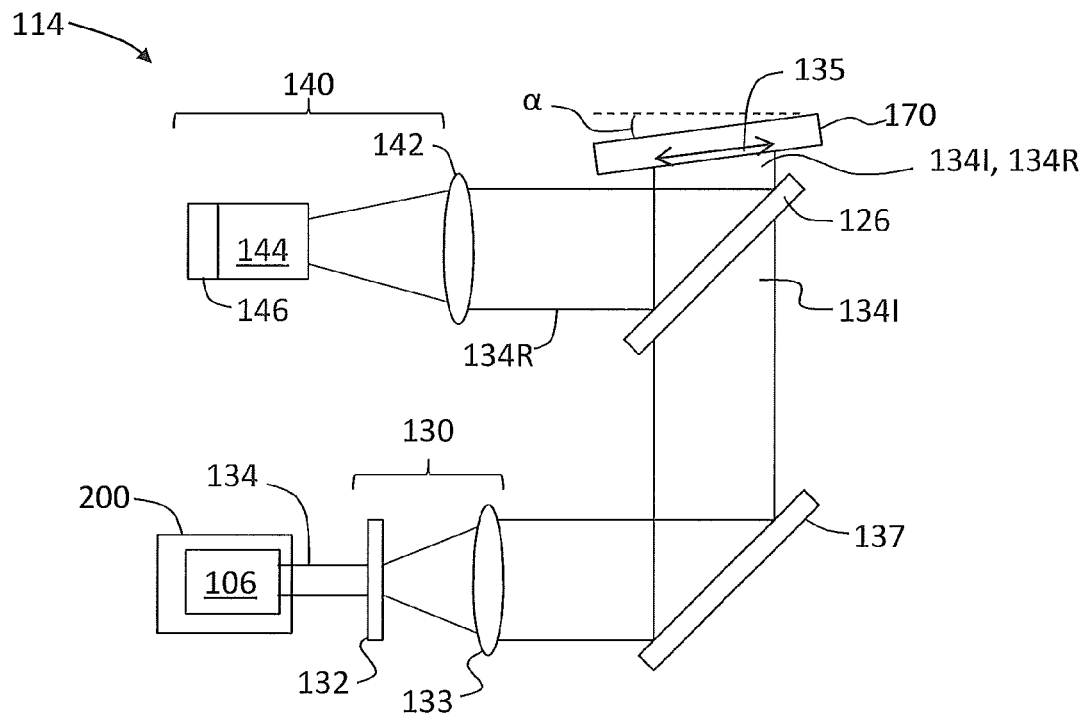
FIG. 7A through FIG. 7D illustrate different embodiments of an optical imager of the optical reader system of FIG. 1.

Four exemplary imaging systems 114 and their operation are now discussed with respect to FIG. 7A through FIG. 7D. In FIG. 7A, the imaging system 114 has a normal to near-near normal incident angle α at microplate 170, where illumination optical system 130 includes a lens or lens system 132 that receives tunable light beam 134 and directs it toward a collimating lens 133. The collimating lens 133 forms from tunable light beam 134 collimated incident light beam 134I that serves as an interrogation beam, and directs this beam toward a fold mirror 137. The fold mirror 137 reflects collimated interrogation beam 134I such that it travels through light-deflecting element 126 and illuminates a predetermined number of RWG biosensors 102 located within the wells 175 of microplate 170 over area 135. Alternatively, illumination optical system 130 is configured to form multiple interrogation beams 134I, where each interrogation beam illuminates a corresponding RWG biosensor 102 located within one of the wells 175 of microplate 170. In addition, optical imager 140 has a telecentric imaging lens 142 with a field of view selected to collect an image 145 from the illuminated RWG biosensor(s) 102.

Figure 7B:
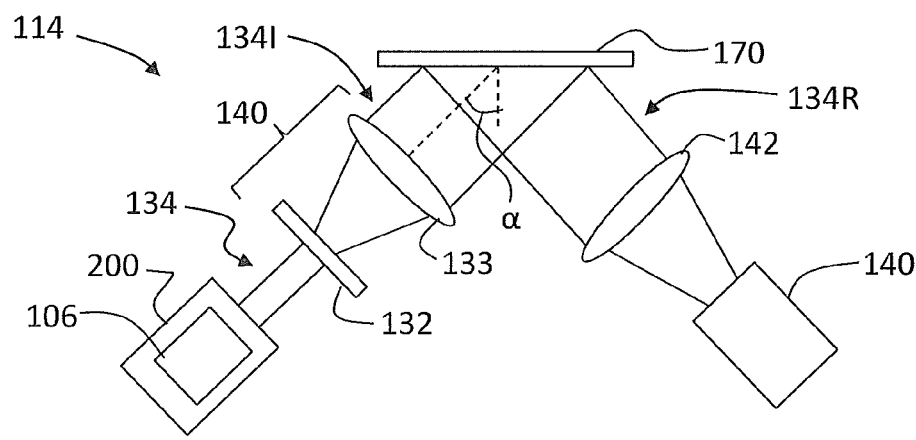

FIG. 7B is a schematic diagram of an example imaging system 114 wherein incident optical beam 134I has an oblique (i.e., non-normal) incidence angle α. The non-normal incidence angle α eliminates the need for light-deflecting element 126 and can improve the optical efficiency by a factor of four. In this embodiment, illumination optical system 130 includes lens 132 that receives tunable light beam 134 and directs it at a predetermined angle toward collimating lens 133. The collimating lens 133 receives tunable light beam 134 and outputs collimated interrogation beam 134I that illuminates a predetermined number of RWG biosensors 102 located within wells 175 of microplate 170. Alternatively, illumination optical system 130 can be configured to form multiple interrogation beams 134I, where each interrogation beam illuminates a corresponding RWG biosensor 102. In addition, optical imager 140 has a telecentric imaging lens 142 positioned at a predetermined angle and having a field of view selected to collect an image 145 from illuminated RWG biosensor(s) 102.

Figure 7C:
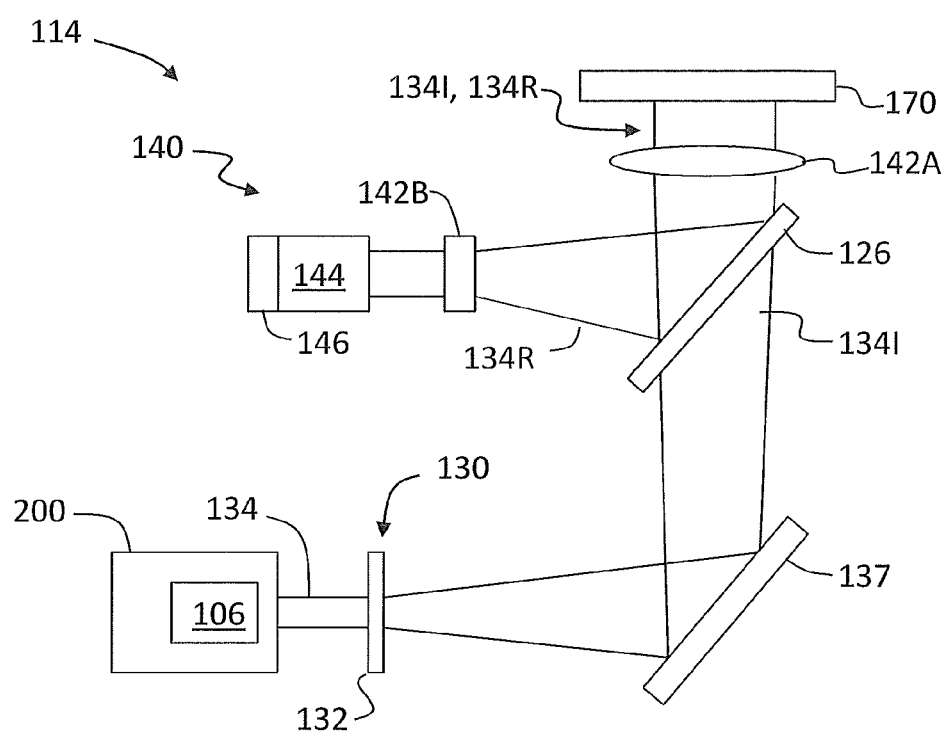

Referring to FIG. 7C, there is shown an exemplary imaging system 114 having a relatively small footprint because illumination optical system 130 and optical imager 140 share a front lens (or lens group) 142A of telecentric imaging lens 142. In this embodiment, lens 132 of illumination optical system 130 receives tunable light beam 134 and directs it in a diverging manner to fold mirror 137. The fold mirror 137 reflects divergent tunable light beam 134 such that it travels through light-deflecting element 126 and to front lens 142A. The front lens 142A forms interrogation beam 134I that illuminates a predetermined number of biosensors 102 located within wells 175 of microplate 170. The front lens 142A also collects reflected light 134R and directs it to light-deflecting element 126. The light-deflecting element 126 directs reflected light 134R toward a lens 142B, which images reflected light 134R onto image sensor 144 as discussed above.

Figure 7D:
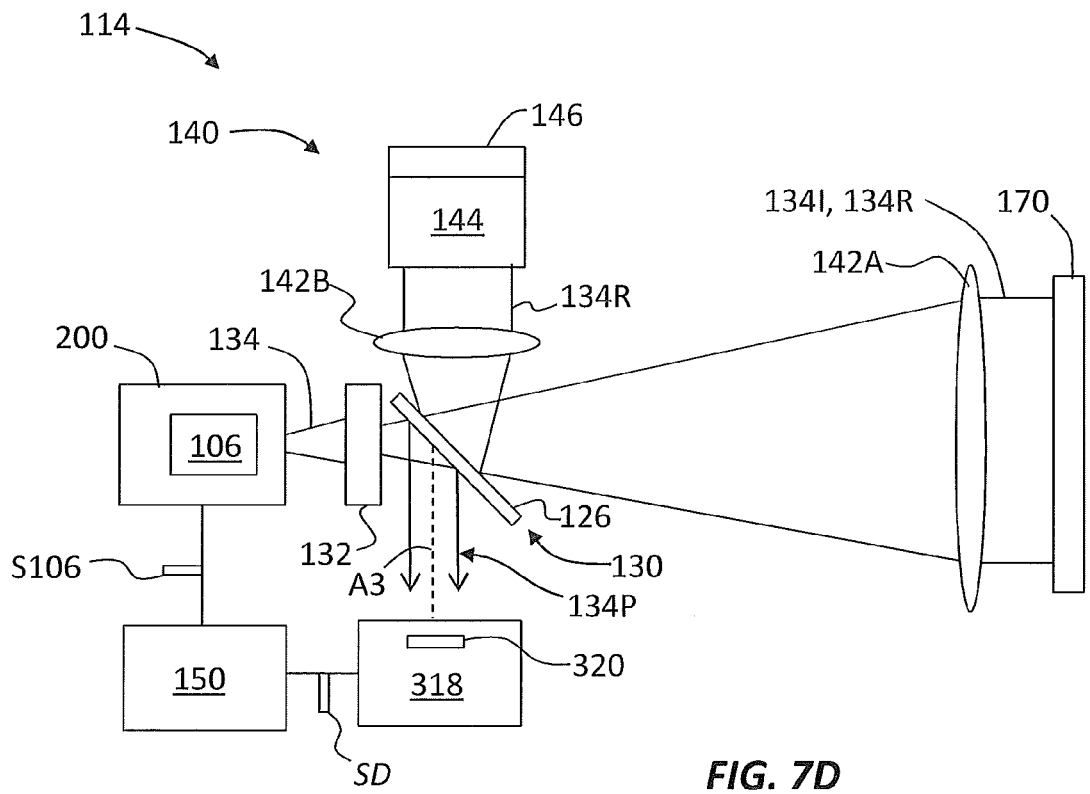

FIG. 7D is a schematic diagram of an example imaging system 114 where illumination optical system 130 and optical imager 140 share front lens 142A of telecentric imaging lens 142. The lens 132 of illumination optical system 130 receives tunable light beam 134 and directs it through light-deflecting element 126 toward front lens 142A via fold mirror 137. The front lens 142A collimates tunable light beam 134 and forms interrogation beam 134I. The front lens 142A also collects reflected light 134R from microplate 170 and RWG biosensors 102 therein and directs it back to light-deflecting element 126 via fold mirror 137. The light-deflecting element 126 then directs reflected light 134R to second lens 142B of optical imager 140 and images reflected light 134R onto image sensor 144 as discussed above.

The imaging system 114 of FIG. 7D shows an example of how light-deflecting element 126 is used to create a tunable light beam portion 134P by deflecting a portion of tunable light beam 134 along an axis A3 toward an example detector system 318. The detector system 318 is operably connected to controller 150, which in turn is operably coupled to tunable light source 106. The detector system 318 is configured with at least one photodetector 320 and generates at least one electrical detector signal SD, which is provided to controller 150. The at least one electrical detector signal SD includes information representative of the center wavelength $\lambda_C$, as described in greater detail below. The controller 150 is configured to process the at least one electrical detector signal SD to determine the center wavelength $\lambda_C$. The controller 150 is also configured to control tunable light source 106 with a light-source signal S106. This particular configuration for light-deflecting element 126 has the advantage that very little if any of the light in tunable light beam 134 is wasted.

Figure 7E:
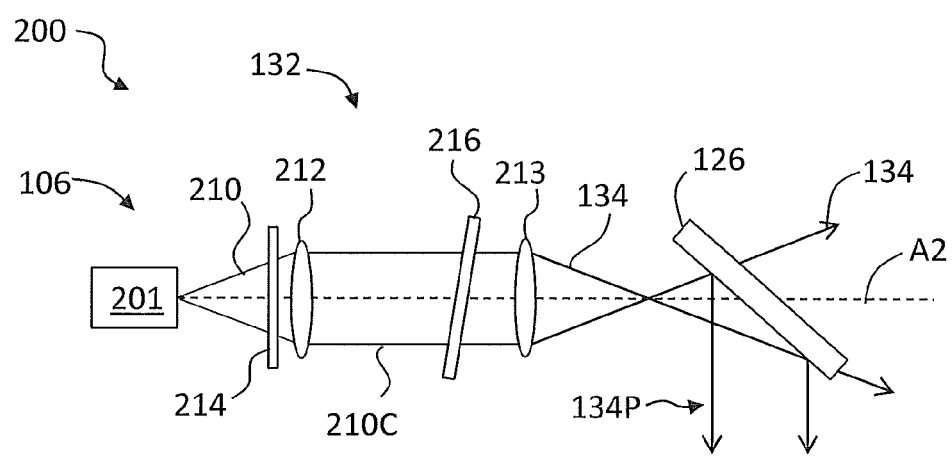
FIG. 7E is a close-up view of an example lens system for the illumination optical system, wherein the lens system forms a collimated tunable light beam within which the angle-adjustable wavelength filter can be inserted.

FIG. 7E is a close-up view of an example configuration for tunable light source system 200 where lens system 132 includes a collimating lens 212 and a focusing lens 213. Lens system 132 may also include a polarizer 214. The collimating lens 212 is configured to receive diverging broadband light 210 from a broadband light source 201 and form therefrom a collimated broadband light beam 210C. In an example, an angle-adjustable wavelength filter ("filter") 216 is arranged downstream of broadband light source 201 along an optical axis A2 and within collimated broadband light beam 210C. The filter 216 makes an angle ("filter angle") φ relative to collimated broadband light beam 210C, which travels generally parallel to axis A2. The filter 216 transforms collimated broadband light beam 210C into (collimated) tunable light beam 134.

The focusing lens 213 receives the collimated tunable light beam 134 and forms therefrom a focused light beam 134 that first converges and then diverges as it passes through light-deflecting element 126 on its way toward front lens 142A and microplate 170. In an example, lens system 132 includes only collimating lens 212.

Tunable Light Source System with Wavelength Measurement Capability

Figure 8:
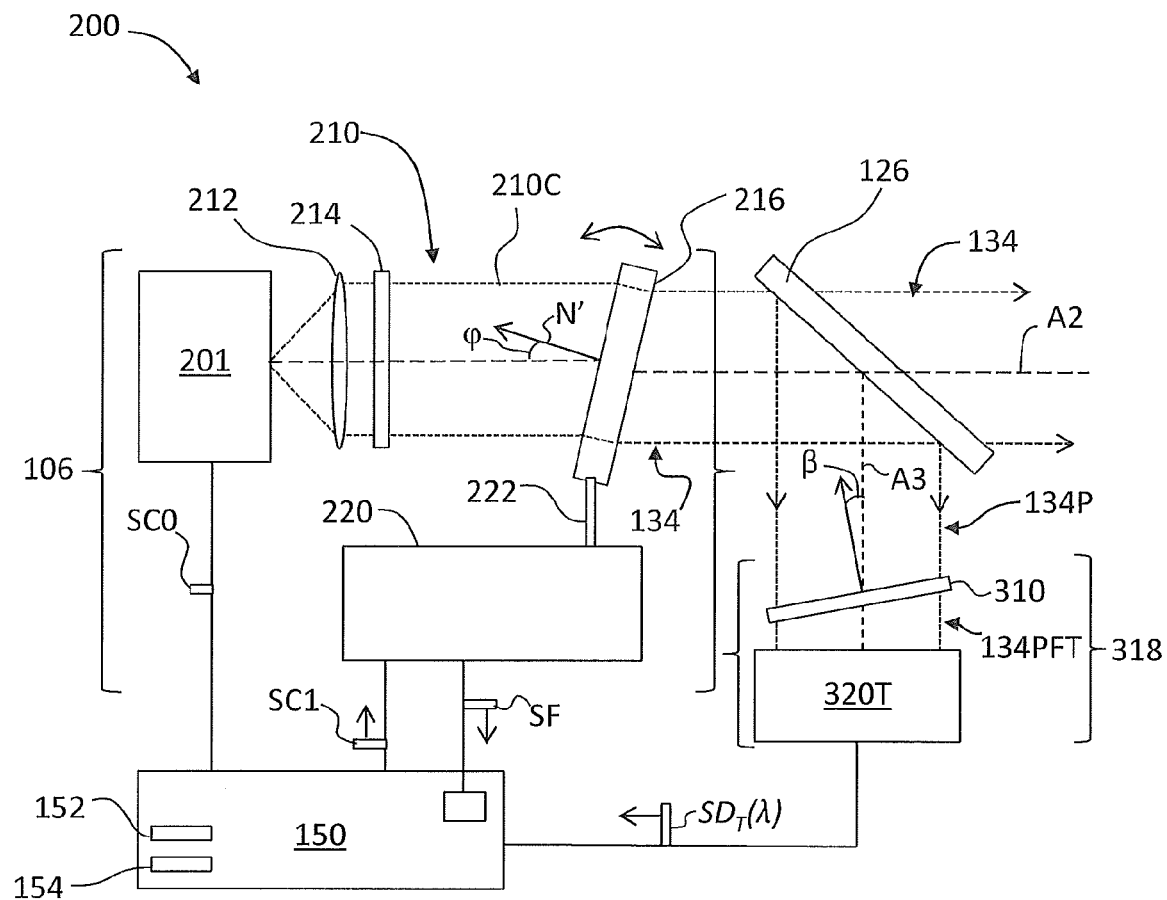
FIG. 8 is a schematic diagram of an example tunable light source system that is configured to measure the center wavelength $\lambda_C$ of the tunable light beam and that employs a detector system having a transmissive reference filter and a single photodetector.

FIG. 8 is a schematic diagram of an example tunable light source system 200 that is configured to measure the center wavelength $\lambda_C$ in tunable light beam 134 during the operation of system 100, i.e., during the biosensor measurement process. The tunable light source system 200 includes tunable light source 106 operably connected to controller 150. The tunable light source 106 emits tunable light beam 134 along optical axis A2. The tunable light beam 134 has the aforementioned tunable center wavelength $\lambda_C$ and in an example its spectral shape $L(\lambda, \lambda_C)$ stays substantially constant even as the center wavelength is tuned (adjusted), so that $L(\lambda, \lambda_C) \approx L(\lambda - \lambda_C)$.

The tunable light source system 200 includes light-deflecting element 126 arranged along or adjacent optical axis A2 so that it defines an optical axis A3, which forms an angle (e.g., a right angle) with optical axis A2. In an example, light-deflecting element 126 is a beam splitter that partially reflects an amount (i.e., a portion of) of tunable light beam 134 incident thereon and transmits the rest of the tunable light beam. In another example embodiment, light-deflecting element 126 is a mirror that is partially inserted into the optical path of tunable light beam 134. Generally, light-deflecting element 126 is configured to deflect at least a portion of tunable light beam 134. In an example, light-deflecting element 126 can be inserted into and removed from the optical path of tunable light beam 134 as required.

A reference band-pass filter or edge-filter (hereinafter, "reference filter") 310 is arranged along optical axis A3, and a transmission photodetector 320T is arranged downstream of the reference filter also along optical axis A3. The reference filter 310 has transmission (filter) function $SR_T(\lambda)$ and is either a low-pass filter or high-pass filter, with a wide-band transition of $\Delta\lambda_R$ from $\lambda_L$ to $\lambda_R$ sufficient to include the wavelength range of tunable light source system 200 used by system 100. The transmission photodetector 320T is electrically connected to controller 150.

In an example, reference filter 310 is placed at an angle β to axis A3 and is an operating parameter of reference filter 310 that is specified as part of the design of tunable light-source system 200 (i.e., when procuring or fabricating the reference filter). In one example, β=0 degrees. In another example, β=45 degrees.

In an example, tunable light source 106 includes a broadband light source 201, such as a superluminescent diode (SLD), as available from Superlum Diodes, Ltd., Moscow, Russia. An example SLD light source 201 has a spectral bandwidth W of 20 nm and a center wavelength $\lambda_C$ of about 840 nm. A conventional broadband LED can also be used as broadband light source 201, provided that the light is sufficiently collimated. The broadband light source 201 emits broadband light beam 210 along optical axis A2. In embodiments, broadband light source 201 has a spectral bandwidth in the range of 10 nm to 45 nm.

With continuing reference to FIG. 8, the tunable light source 106 also includes the aforementioned filter 216 arranged downstream of broadband light source 201 along optical axis A2 in collimated broadband light beam 210C. The filter angle φ is measured relative to a surface normal N' of the filter and axis A2. In an example, filter 216 is mechanically connected to an angle-adjustment unit 220 configured to control the filter angle φ. Example angle-adjustment units 220 are discussed below.

The filter 216 is configured to transmit light over a spectral band-pass (linewidth) $\Delta\lambda_T$ having a center wavelength $\lambda_C$. The "tunability" of filter 216 refers to its ability to adjust the center wavelength $\lambda_C$ as a function of filter angle φ while maintaining the spectral linewidth $\Delta\lambda_T$ of the tunable light beam 134 as sufficiently narrow. Thus, filter 216 has a reference-filter function $L(\lambda, \lambda_C)$ that essentially shifts along with the center wavelength $\lambda_C$. The broadband light beam 210 travels through tunable filter 216 and becomes the aforementioned narrow-band tunable light beam 134 that has a tunable light beam spectrum $L(\lambda, \lambda_C)$ with the aforementioned spectral linewidth $\Delta\lambda_T$. In the case where the spectrum $L(\lambda, \lambda_C)$ of tunable light beam 134 does not substantially change shape but merely shifts along with the center wavelength $\lambda_C$, the tunable light beam spectrum can be expressed as $L(\lambda - \lambda_C)$.

As discussed above in connection with FIG. 7E, tunable light source 106 may also include polarizer 214 arranged along optical axis A2, e.g., between broadband light source 201 and filter 216, to linearly polarize broadband light beam 210 to have P-polarization or S-polarization. In some cases, an S-polarization configuration for polarizer 214 is used because it can be used over a wider range of incident beam angles. The tunable light source 106 may also include collimating lens 212 disposed along optical axis A2 adjacent broadband light source 201 to form collimated broadband light beam 210C.

The filter angle φ is adjusted by controller 150 sending a control signal SC1 to angle-adjustment unit 220, which in response adjusts the position (angle) of filter 216. The angle-adjustment unit 220 may also send back to a data acquisition board 158 in controller 150 a feedback signal SF representative of a wavelength tuning parameter x that provides the filter angle adjustment. The wavelength tuning parameter x may be, for example, a mechanical position, a voltage, a current, etc., depending on the type of wavelength tuning mechanism used in tunable light source 106. In an example, the wavelength tuning parameter x is representative of the filter angle φ. The wavelength tuning parameter x is useful to have in controller 150 because it can be related to the measured central wavelength $\lambda_C$ provided to the controller via the at least one detector signal $SD(\lambda_C)$.

In the operation of tunable light source system 200 of FIG. 8, controller 150 sends a control signal SC0 to tunable light source 106 and in particular to broadband light source 201 therein, which causes the broadband light source to emit broadband light beam 210.

The broadband light beam 210 travels along axis A2 and passes through filter 216, which as described above forms tunable light beam 134 having a center wavelength $\lambda_C$ and a spectrum $L(\lambda, \lambda_C)$. The tunable light beam 134 then encounters light-deflecting element 126, which deflects the aforementioned portion 134P of the tunable light beam to travel along axis A3. The tunable light beam portion 134P then travels through (i.e., is transmitted by) reference filter 310, which forms a transmitted, filtered light beam portion 134PFT that is detected by transmission photodetector 320T. In response, transmission photodetector 320T generates electrical transmission-detector signal $SD_T(\lambda_C)$ representative of the detected intensity of transmitted, filtered light beam portion 134 PFT as a function of the tuned (i.e., changing) center wavelength $\lambda_C$. The electrical detector signal $SD_T(\lambda_C)$ is then directed to and received by controller 150.

Figure 9:
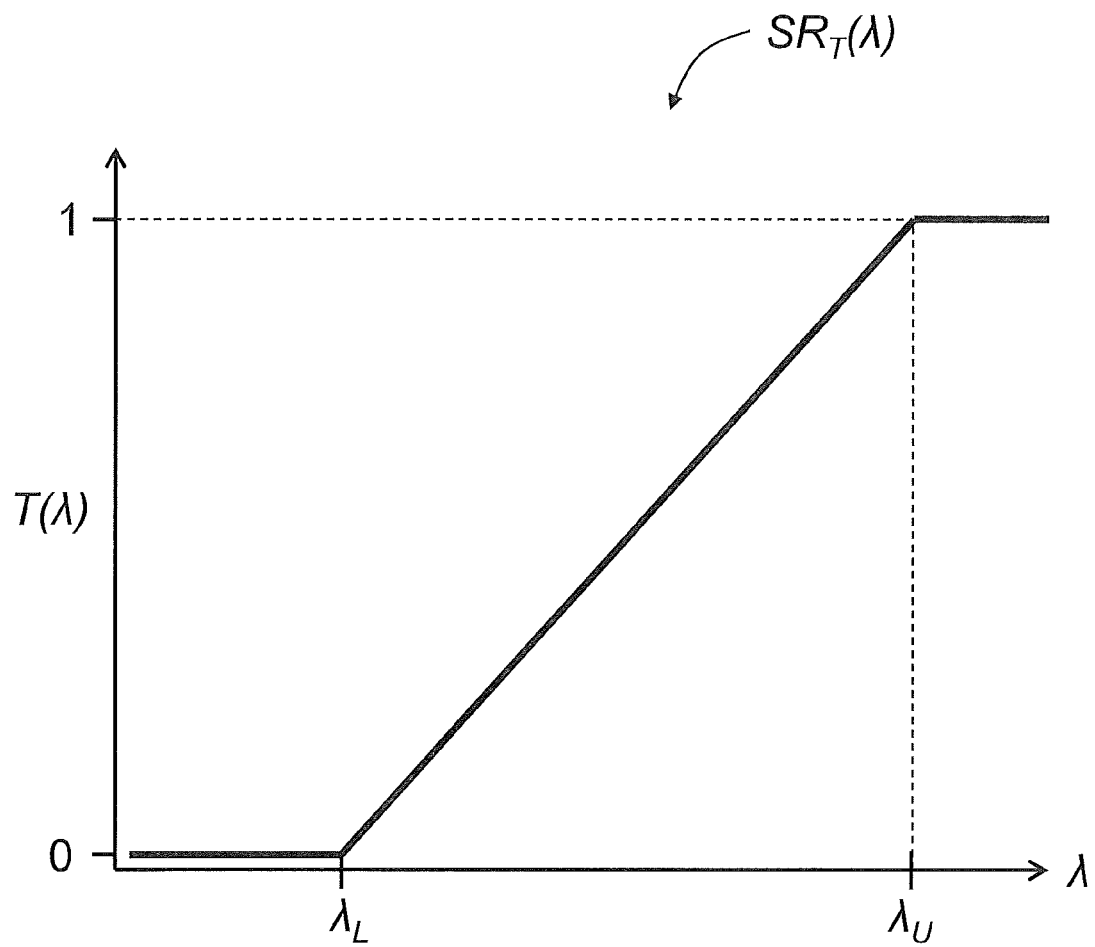
FIG. 9 shows an example reference-filter function $SR_T(\lambda)$ for the transmissive reference filter of FIG. 8 as a plot of the reference-filter transmission $T(\lambda)$ versus wavelength.

FIG. 9 plots the transmission $T(\lambda)$ versus wavelength and illustrates an example reference-filter function $SR_T(\lambda)$ for transmission reference filter 310. The reference filter 310 is essentially a low-pass filter or a high-pass filter with wideband transition between a lower wavelength $\lambda_L$ and an upper wavelength $\lambda_U$. In an example, reference filter 310 has a slow cutoff rate as defined by the slope $m_T$ of the filter curve, e.g., $m_T = 1/(\lambda_U - \lambda_L)$ for the example of FIG. 9. Note that the reference-filter transition bandwidth is $\Delta\lambda_R = (\lambda_U - \lambda_L)$.

The reference filter 310 with a select reference-filter function $SR_T(\lambda)$ is available from Iridian Spectral Technologies of Ottawa, Canada. A notable characteristic of reference-filter function $SR_T(\lambda)$ of FIG. 9 is that the transmittance T changes smoothly from a lower wavelength $\lambda_L$ where the transmission $T(\lambda_L)$ is substantially opaque, to a high value at an upper wavelength $\lambda_U$, where the transmission $T(\lambda_U)$ is substantially clear. In the example reference-filter function $SR_T(\lambda)$ of FIG. 9, the reference-filter is a high-pass filter and the transmission curve is linear. However, it is noted that in general the transition in transmission $T(\lambda)$ only needs to be monotonically increasing between lower wavelength $\lambda_L$ and an upper wavelength $\lambda_U$.

Figure 10:
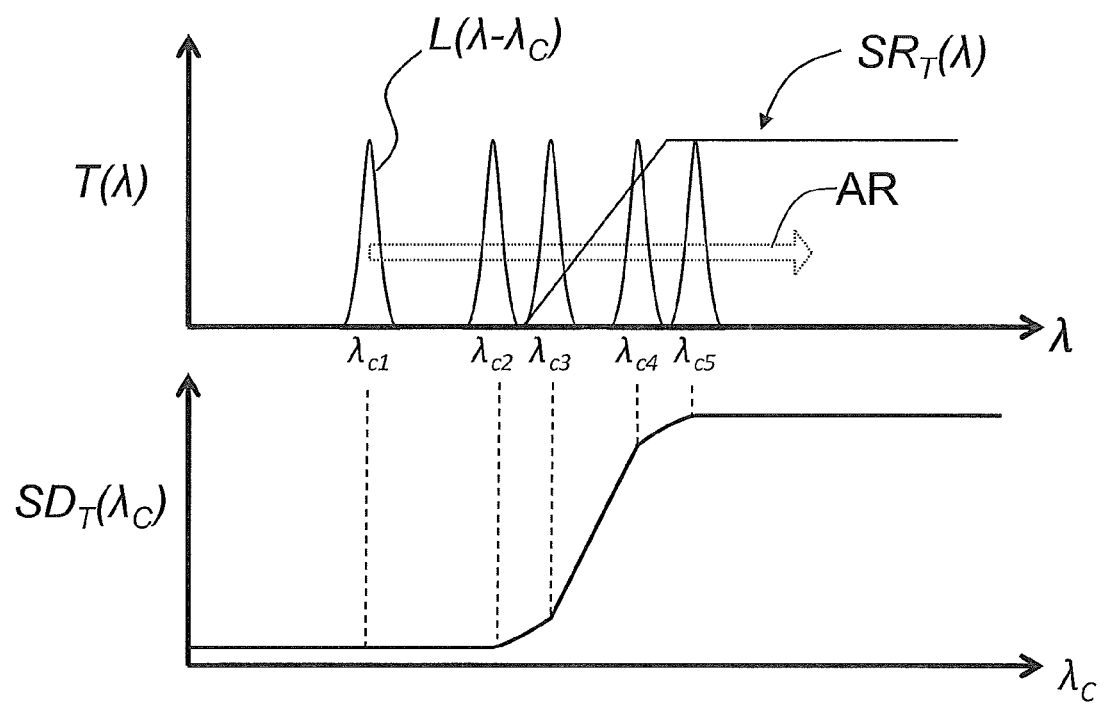
FIG. 10 shows a representative electrical transmission-detector signal $SD_T(\lambda_C)$ for the tunable light source of FIG. 8 for a series of wavelength tuning positions (and thus a series of center wavelengths $\lambda_{C1}$, $\lambda_{C2}$, ... $\lambda_{CS}$) relative to the reference-filter function $SR_T(\lambda)$ of FIG. 9.

FIG. 10 shows a representative electrical transmission-detector signal $SD_T(\lambda_C)$ for tunable light source system 200 of FIG. 8 for a series of wavelength tuning positions (and thus a series of center wavelengths $\lambda_{C1}, \lambda_{C2}, \ldots \lambda_{C5}$) relative to the reference-filter function $SR_T(\lambda)$ of FIG. 9. An arrow AR shows the shift in the tunable light beam spectrum $L(\lambda - \lambda_C)$ as the center wavelength $\lambda_C$ is adjusted. In an example, if the tunable light beam spectrum $L(\lambda - \lambda_C)$ is truly monochromatic (that is, $\Delta L_T = 0$), then the shape of the electrical transmission-detector signal $SD_T(\lambda_C)$ as a function of center wavelength $\lambda_C$ will be the same as that of the reference-filter function $SR_T(\lambda)$ of reference filter 310.

When the spectrum $L(\lambda - \lambda_C)$ of tunable light beam 134 has a smooth shape, such as a Gaussian or a Lorentzian shape, then the electrical transmission-detector signal $SD_T(\lambda_C)$ has a similar shape to reference-filter function $SR_T(\lambda)$ with smoothed edges, as shown in the detector signal curve of FIG. 10. However, when the width $\Delta\lambda_T$ of the spectrum $L(\lambda - \lambda_C)$ is sufficiently narrow (e.g., 1 nm to 2 nm), then the smoothing of the electrical transmission-detector signal $SD_T(\lambda_C)$ is minimal. This allows the electrical transmission-detector signal $SD_T(\lambda_C)$ to be used to measure the center wavelength $\lambda_C$ of tunable light beam 134 as the tunable light beam is tuned by adjusting the filter angle $\phi$ of filter 216.

Figure 11:
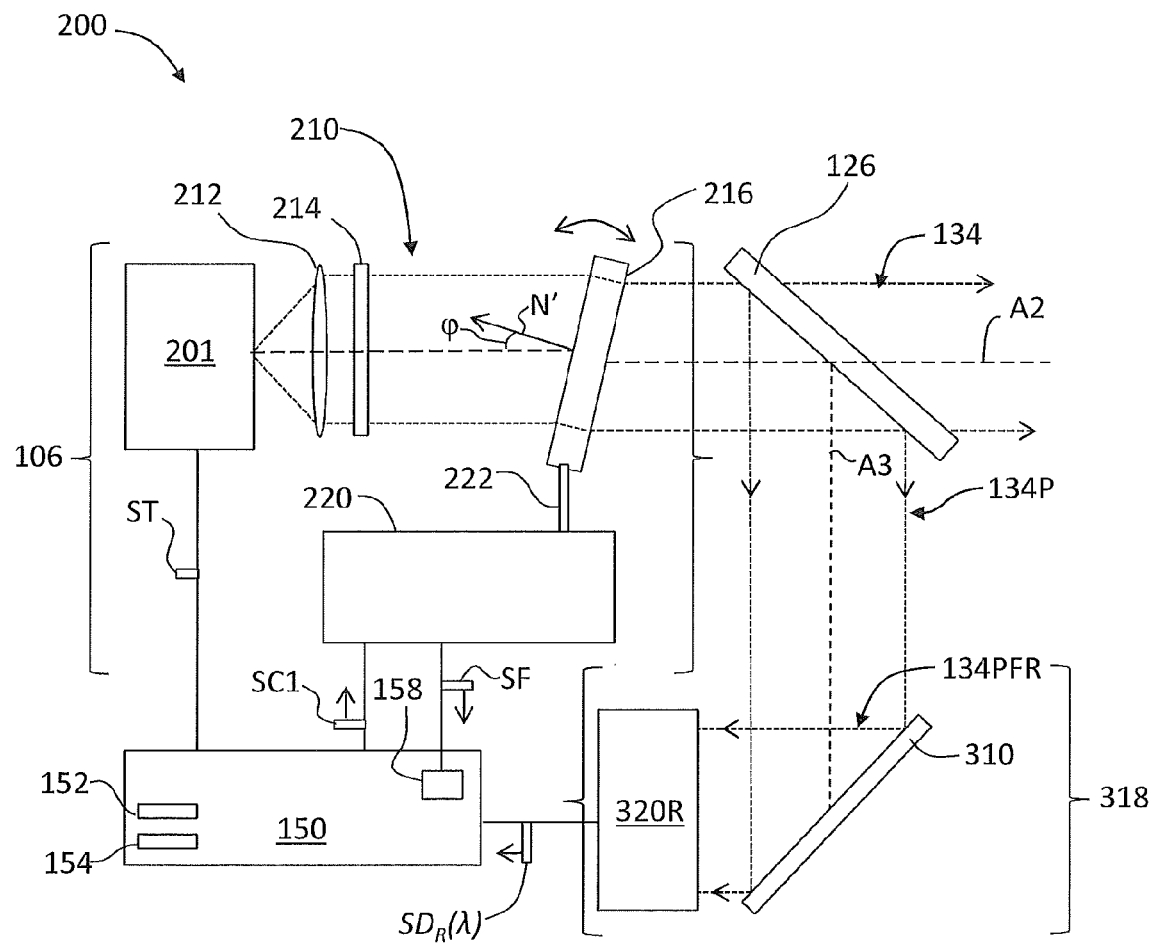
FIG. 11 is similar to FIG. 8 and illustrates an example tunable light source where the detector system includes a reflective reference filter rather than a transmissive reference filter.

FIG. 11 is similar to FIG. 8 and illustrates an example tunable light source system 200 where detector system 318 has a reference filter 310 that is reflective rather than transmissive. The tunable light beam portion 134P reflects from reflective reference filter 310, which forms a reflected, filtered light beam portion 134PFR that is detected by a reflection photodetector 320R. In response, reflection photodetector 320R generates an electrical reflection-detector signal $SD_R(\lambda_C)$ that is representative of the detected intensity of reflected, filtered light beam portion 134PFR as a function of the tuned (i.e., changing) center wavelength $\lambda_C$. The electrical reflection-detector signal $SD_R(\lambda_C)$ is directed to and received by controller 150 for processing.

Figure 12:
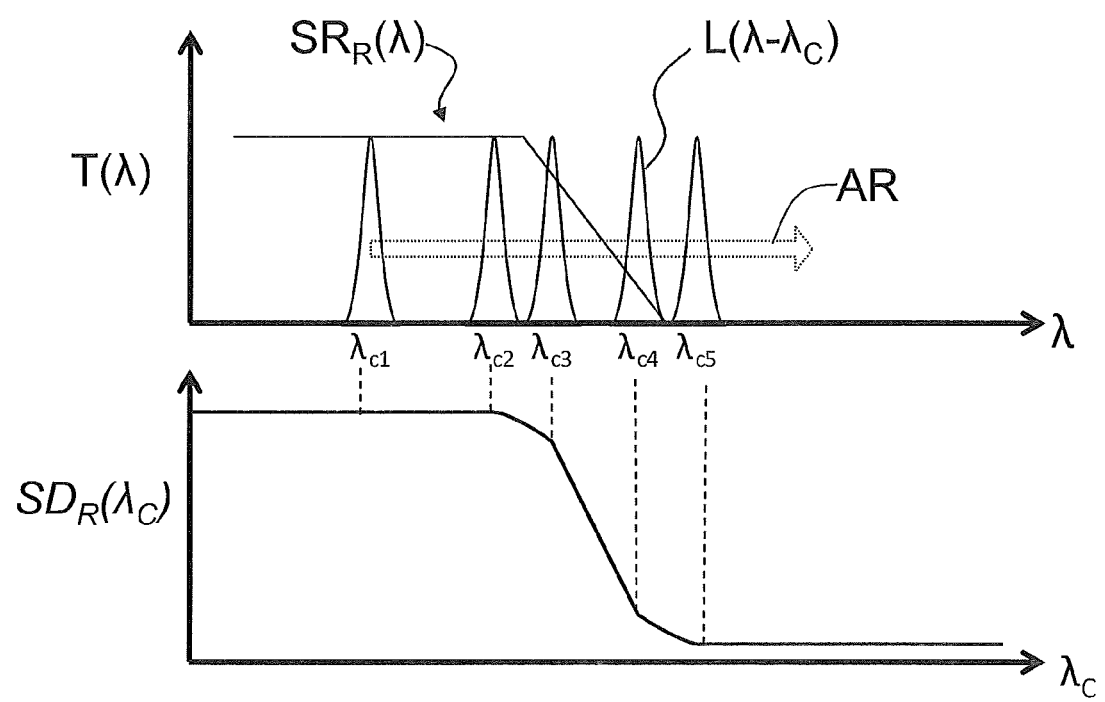
FIG. 12 is similar to FIG. 10 and plots a reference-filter function spectrum $SR_R(\lambda)$ along with an electrical reflection-detector signal $SD_R(\lambda_C)$ for the configuration of the tunable light source of FIG. 8.

FIG. 12 is similar to FIG. 10 and plots the reference-filter function $SR_R(\lambda)$ along with the electrical reflection-detector signal $SD_R(\lambda_C)$ for the configuration of tunable light source system 200 of FIG. 11. In this embodiment, reflective reference filter 310 serves as a reflective low-pass or high-pass filter with a reflectance spectrum $SR_R(\lambda)$ related to the reference-filter function $SR_T(\lambda)$ by the equation $SR_R(\lambda) \approx 1 - SR_T(\lambda)$. Electrical reflection-detector signal $SD_R(\lambda_C)$ thus shows a negative-slope where electrical transmission-detector signal $SD_T(\lambda_C)$ obtained by transmission shows a positive-slope (and vice-versa). Electrical reflection-detector signal $SD_R(\lambda_C)$ has the same properties as detector signal $SD_T(\lambda_C)$ and can be used to find the center wavelength $\lambda_C$ in an analogous fashion. In a further example, where transmission reference filter 310 has a low-pass transmission spectrum, the roles of detectors 320T and 320R are reversed.

Figure 13:
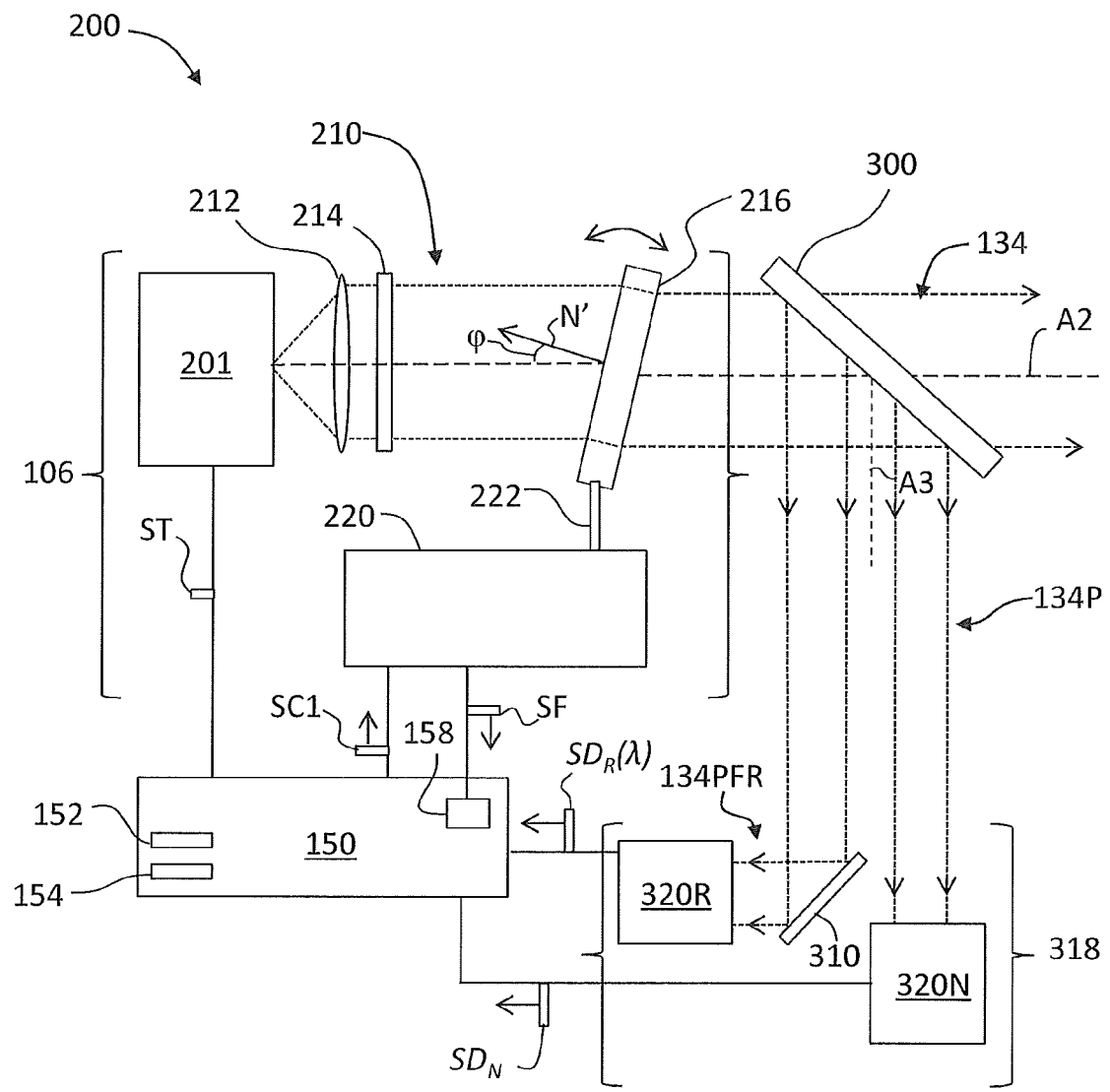
FIG. 13 is similar to FIG. 8 and illustrates an example tunable light source system where the detector system is configured to measure the overall intensity of the tunable light beam portion.

FIG. 13 is similar to FIG. 11 and illustrates an example tunable light source system 200 where detector system 318 has a reflective reference filter 310, but the reference filter extends only part way into the optical path of tunable light beam portion 134P. Consequently, some of tunable light beam portion 134P travels straight to normalization detector 320N without passing through reference filter 310. However, some of tunable light beam portion 134P reflects from reflective reference filter 310 and forms reflected, filtered tunable light beam portion 134FPR.

In this embodiment, normalization photodetector 320N generates a normalization detector signal $SD_N$ representative of the intensity of tunable light beam portion 134P, while reflection photodetector 320R generates the aforementioned electrical reflection-detector signal $SD_R(\lambda_C)$ from reflected, filtered tunable light beam portion 134FPR.

The controller 150 receives both electrical reflection-detector signal $SD_R(\lambda_C)$ and normalization detector signal $SD_N$ and forms a normalized electrical reflection-detector signal $SD_{RN}(\lambda_C) = SD_R(\lambda_C)/SD_N$. The normalized electrical reflection-detector signal $SD_{RN}(\lambda_C)$ is independent of variations the overall intensity of filtered tunable light beam portion 134P. In an example, the system is calibrated so that the normalized electrical reflection-detector signal $SD_{RN}(\lambda_C)$ ranges from 0 to 1. This is accomplished by offsetting reflection-detector signal $SD_R(\lambda_C)$ so that it has zero signal at high wavelength (or low wavelength for a low-pass design). The normalized electrical reflection-detector signal $SD_{RN}(\lambda_C)$ is also offset so that it has zero signal where there is no light incident thereon.

It is noted here that the tunable light-source system 200 of FIG. 8 can be modified to include a normalization detector 320N as well as a transmission detector 320T in a similar manner to the tunable light-source system 200 of FIG. 13.

Figure 14:
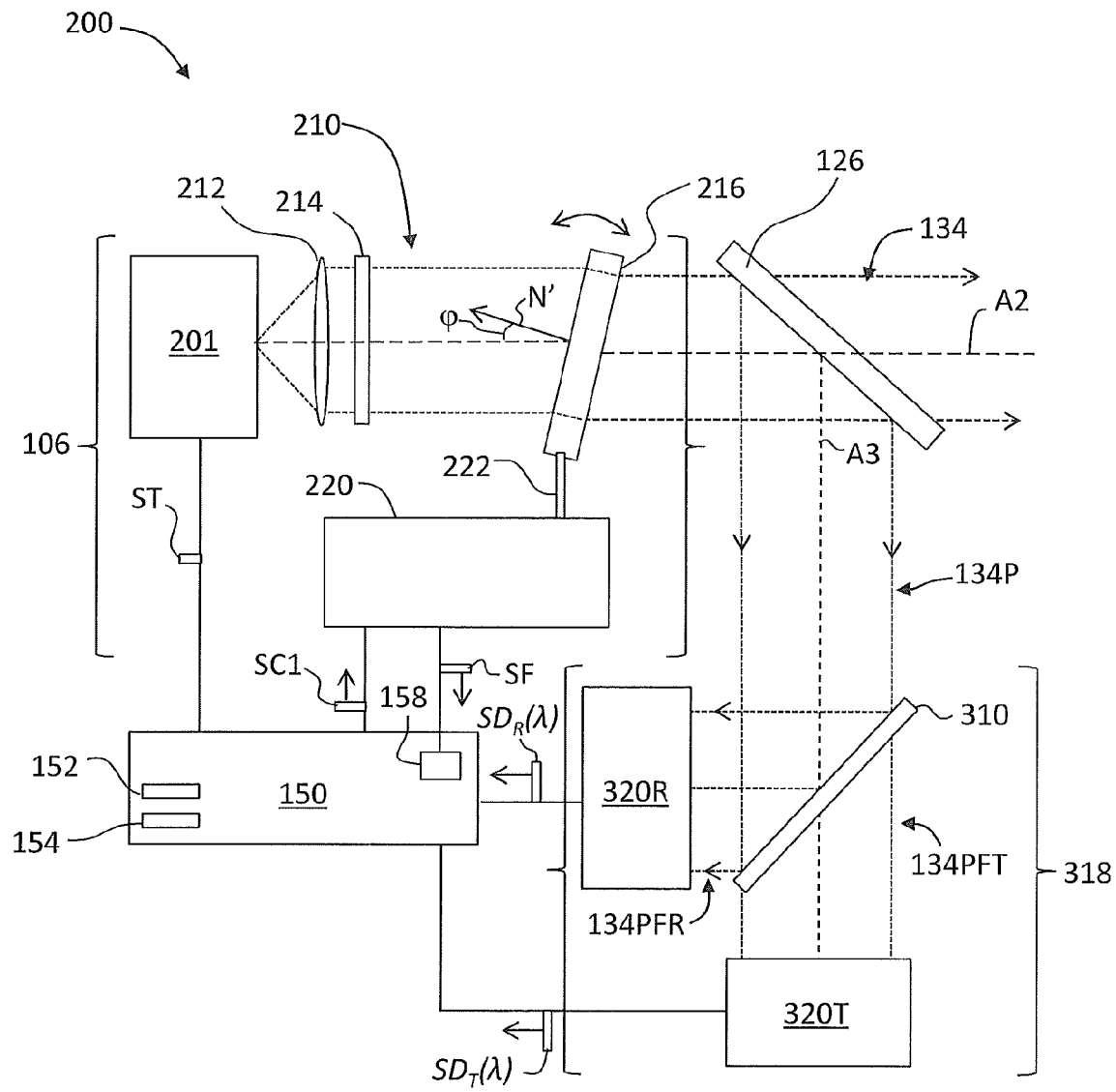
FIG. 14 is similar to FIG. 13 and illustrates an example tunable light source system where the detector system includes a reference filter that is partially reflective and partially transmissive and that resides in the optical path of the tunable light beam portion, with reflection and transmission photodetectors arranged to detect the reflected and transmitted filtered tunable light beam portions, respectively.

FIG. 14 is similar to FIG. 13 and illustrates an example tunable light source system 200 where reference filter 310 of detector system 318 is partially reflective and partially transmissive. The reference filter 310 resides in the optical path of tunable light beam portion 134P, e.g., all of the tunable light beam portion is incident up the reference filter. Consequently, some of tunable light beam portion 134P travels through reference filter 310 and to transmission photodetector 320T as transmitted filtered light beam portion 134PFT.

The rest of tunable light beam portion 134P reflects from reference filter 310 to detector 320R as reflected filtered light beam portion 134PFR. Thus, transmission photodetector 320T generates the aforementioned electrical transmission-detection signal $SD_T(\lambda_C)$, while reflection photodetector 320R generates the aforementioned electrical reflection-detector signal $SD_R(\lambda_C)$.

The controller 150 receives both electrical transmission-detector signal $SD_T(\lambda_C)$ and electrical reflection-detector signal $SD_R(\lambda_C)$. This provides tunable light source system 200 with double the reduction in the signal-to-noise ratio (SNR) of configurations that detect only one of the transmitted or reflected filtered tunable light beam portions. In the typical case where absorption is zero or is independent of wavelength λ, the sum of signals $SD_T(\lambda_C)$ and $SD_R(\lambda_C)$ is a close measure of the total amount of tunable light beam portion 134P detected by detector system 318. In this case, a separate and direct measurement of the amount (i.e., intensity) of tunable light beam portion 134P as in the configuration of FIG. 13 is not required. In an example, controller 150 forms a modified detector signal $SD_M(\lambda_C) = \{SD_T(\lambda_C) - SD_R(\lambda_C)\}/\{SD_T(\lambda_C) + SD_R(\lambda_C)\}$.

When electrical transmission-detector signal $SD_T(\lambda_C)$ and electrical reflection-detector signal $SD_R(\lambda_C)$ are each calibrated so the minimum outputs are zero, the modified detector signal $SD_M(\lambda_C)$ is independent of intensity variations in tunable light beam portion 134P. Further, electrical transmission-detector signal $SD_T(\lambda_C)$ and electrical reflection-detector signal $SD_R(\lambda_C)$ are usually calibrated to have the same maximum signal value so that the modified detector signal $SD_M(\lambda_C)$ scales between −1 and 1.

Figure 15:
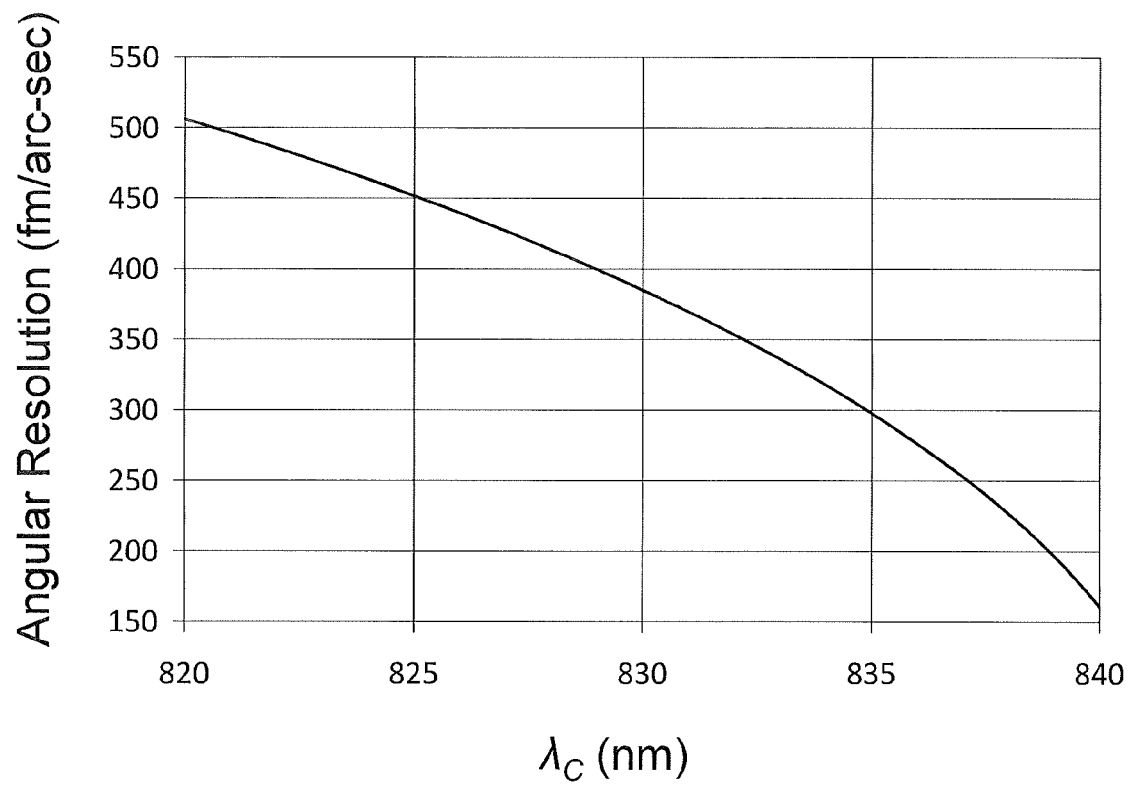
FIG. 15 plots the angular resolution $d\lambda_C/d\phi$ (fm/arc-sec) versus center wavelength $\lambda_C$ (nm) and illustrates the sensitivity of the change in the center wavelength to the tuning angle $\phi$ for a representative angle-adjustable wavelength filter.

FIG. 15 plots the angular resolution $d\lambda_C/d\phi$ (fm/arc-sec) versus the center wavelength $\lambda_C$ (nm) and illustrates the sensitivity of the center wavelength to the tuning angle φ for a representative interference filter 216. The plot indicates the aforementioned repeatability requirement of ±1 pm, which corresponds to approximately ±3 arc-seconds, or less than 0.001°.

Averaging across pixels in image sensor 144 may not increase system performance, as each pixel in the system typically is subject to the same wavelength error. Averaging methods of peak wavelength detection (such as centroid methods) may reduce system sensitivity to this type of measurement error if the error varies randomly for each frame. However, it may not reduce sensitivity where the error has other distributions, such as a fixed offset for each series of images. In practice, unidirectional knowledge of the center wavelength to the tuning angle φ in the order of ±2 arc-secs is sought.

In an example embodiment of tunable light source system 200, electrical transmission-detector signal $SD_T(\lambda_C)$, electrical reflection-detector signal $SD_R(\lambda_C)$, modified detector signal $SD_M$, normalization detector signal $SD_N$, or the appropriate combination of these signals is generated substantially simultaneously with the reading of biosensor 102 using system 100 and the central wavelength $\lambda_C$ as determined from the measured detector signal.

At the end of the biosensor scan, there are two sets of measurements: the biosensor measurements (i.e. optical images of the biosensors) and the measurements of central wavelength $\lambda_C$ as determined by the at least one detector signal SD. Each biosensor measurement is matched to the corresponding measurement of the central wavelength $\lambda_C$ used in the biosensor measurement.

Figure 16:
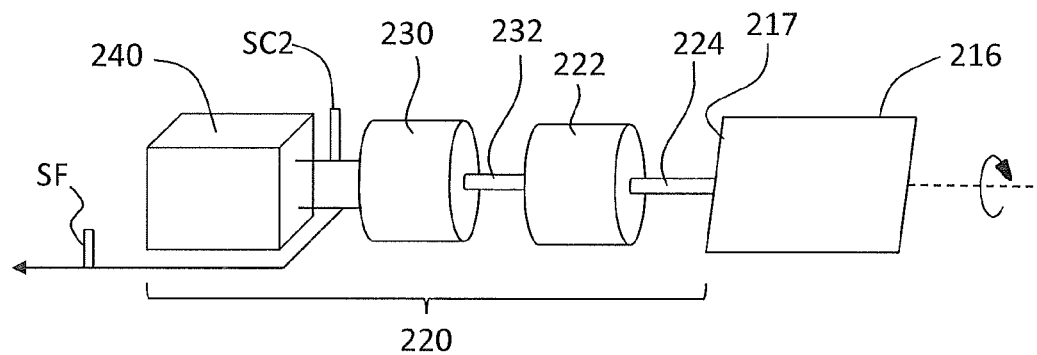
FIG. 16 is a schematic side elevation view of an example angle-adjustment unit that includes a gear box, a gear motor, and a motor controller.

FIG. 16 is a schematic side elevation view of an example angle-adjustment unit 220 that includes a gear box 222 with a drive shaft 224 operably connected to filter 216 at a side 217. The angle-adjustment unit 220 also includes a motor 230 mechanically connected to gear box 222 via a drive shaft 232. The motor 230 can thus be called a "gear motor." The angle-adjustment unit 220 further includes a motor controller 240 electrically connected to motor 230. In an example, motor 230 provides a wavelength tuning parameter in the form of "clicks" or encoder lines per revolution, with each click corresponding to a discrete positional (rotational) increment of drive shaft 232. Further, gear box 222 has a gear ratio R that in an example is relatively high (e.g., R≥1,000) so that it greatly expands the number of clicks per revolution of drive shaft 224 of the gear box.

An example motor 230 suitable for use in angle-adjustment unit 220 is the model 1524-SR brushed DC motor containing a model IE-512 quadrature encoder, both from Dr. Fritz Faulhaber GmbH & Co. KG of Stuttgart, Germany. An example motor controller 240 is the model MCDC3006S, and an example gearbox 222 is the model 15/8 gearbox, both also from Dr. Fritz Faulhaber GmbH & Co. KG. In an example, motor 230 has 2,048 clicks per revolution and gearbox 222 has a gear ratio R of 1670:1. The number of clicks per degree is given by 2,048×1,670/360=9,500 clicks/degree. An example angular sweep length is 15 degrees centered on 832 nm. The average wavelength increment per click is 98.2 femtometers, or about 0.0001 nm. In an example, the repeatability of a wavelength sweep is better than a single click.

In an example, motor controller 240 and gear motor 230 have relatively low resolution and low cost (e.g., about ⅕ of a degree, at a present-day cost of about $50) in combination with gearbox 222. The gearbox 222 provides the aforementioned mechanical advantage or gear ratio R, that is, the ratio of motor angular position (x) to filter angle φ.

Although this resolution easily meets the requirements for most configurations of system 100, gearbox 222 may not be predictable from motor output. For example, there may be variation in the lubrication between contact surfaces in between gears, or backlash. All gearboxes 222 have some backlash, even those advertised as having zero backlash. Backlash occurs because only one of the forward-direction or reverse-direction gear contact surfaces can be engaged at a time. There is always some clearance to the other surface, so that when changing motor direction, no gearbox motion occurs until that clearance distance is covered. To achieve best performance, the motor system must be rotated in a single direction without stopping. Even so, filter 216 may "free-wheel" ahead of motor 230 under its own momentum whenever the motor stops or changes direction briefly to correct for a leading motor error. In an example, this issue can be corrected by adding a device that opposes motion such as a spring or damper. However, this increases the system cost.

In an example, gearbox 222 may be omitted, and motor 230 may drive filter 216 directly. An example motor 230 used in this manner is the model 4109Y-51 stepper motor from Lin Engineering, Inc. of Morgan Hill, Calif. In an example, this motor was tested to hold position to a repeatability of ±1.5 pm, close to the required specification. This motor has 400 full steps per revolution, and up to 256 micro steps, or approximate 3.7 pm per micro step, so stepping in increments of 27 steps per image would give approximately 100 pm per frame.

Figure 17:
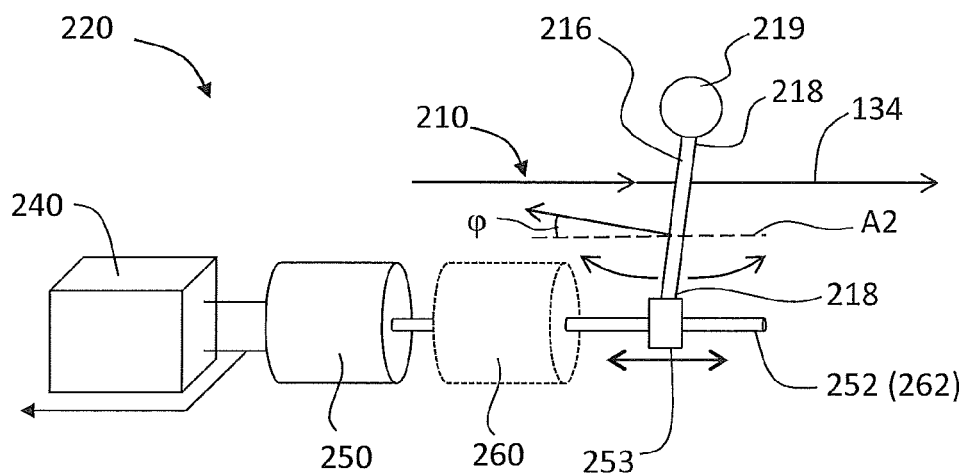
FIG. 17 is similar to FIG. 16 and illustrates another example of an angle-adjustment unit that includes a linear actuator and an angle-adjustable filter that swings on a hinge.

FIG. 17 is a schematic side elevated view of an embodiment of angle-adjustment unit 220. The angle-adjustment unit 220 includes motor controller 240 electrically connected to a motor 250 that has a screw shaft 252. The screw shaft 252 is mechanically connected to filter 216 at or near one of two filter ends 218 via a screw nut 253. A hinge 219 connected to filter 216 at the filter end 218 opposite the filter end 218 to which the screw shaft 252 is connected allows for filter 216 to rotate (swing) as screw shaft 252 is urged to move along its axis by stepper motor 250. In an example, screw shaft 252 may be a ball-screw shaft. A variety of other configurations for angle-adjustment unit 220 that employ different types of adjustment means may also be employed. A gearbox 260 (shown in phantom) with a drive shaft 262 can also be employed to provide improved positional accuracy. In a further example, motor 250, gearbox 260, screw shaft 252 and screw nut 253 may be replaced with a linear stage system containing a linear motor.

With reference to tunable light source system 200 of FIG. 12, in an example, a suitable filter 216 is an interference filter, also known as a dichroic filter. The center wavelength $\lambda_C$ is given by:

$$\lambda_C(\varphi) = \lambda_0 \sqrt{1 - \frac{\sin^2 \varphi}{n^2}}$$

where $\varphi$ is the aforementioned filter angle and n and $\lambda_0$ are constant properties of filter 216. In one embodiment, filter angle $\varphi$ is tuned to 11.5° and within a range of ±7.5° relative to this angle. The band-pass $\Delta\lambda_T$ of filter 216 can vary slightly with the tuning of $\lambda_C$, but in examples the spectral shape $L(\lambda-\lambda_C)$ is well represented by a Gaussian function.

As discussed above, there is a need to control the filter angle $\varphi$ to a high degree of resolution, such as to $1/3,000^{th}$ of a degree. However, angle-adjustment units having such resolution are expensive (presently greater than $1,000) and are also rather large. Thus, tunable light source system 200 as disclosed herein employs a configuration for angle-adjustment unit 220 that utilizes relatively inexpensive components in combination with an absolute reference measurement rather than employing a single expensive high-resolution encoder.

For an angle-adjustment unit 220 that relies on a motor (e.g., gear motor 230 or motor 250) that moves during the measurement process of system 100, it is useful to identify an average location of the motor position that corresponds to the measurement. This calls for tight synchronization of the measurement process and the motor movement.

For a motor that holds filter 216 stationary for each biosensor measurement at a given center wavelength $\lambda_C$, tight synchronization of image capture and wavelength measurement is not required. The measured central wavelength can be used in the calculation for determining the peak in the reflected biosensor signal $LR(\lambda)$ (see FIG. 6) to correct for any uncertainty in the motor position.

In a further example, for a motor that can hold a sufficiently accurate position but that is subject to missing steps, the wavelength measurement need only be half the size of the minimum size of the error motion distance. In this case, the wavelength measurement would not be used in resonant peak calculation, but rather to verify that no error had occurred.

Factors relating to specific modes of operation such as motor speed and direction (backlash) are omitted for clarity. These factors tend to be insubstantial, especially in the case where reference measurements are carried out in the same manner or at the same time as the actual biosensor 102 measurements.

A change in filter angle $\varphi$ with respect to wavelength tuning parameter x is a function of the gear ratio, namely:

$$\frac{d\varphi}{dx} = \frac{1}{R}.$$

The gear ratio R is considered to be constant. Wear and tear in gearbox 222 may affect the wavelength tuning parameter x, but not the (average) gear ratio R. The gear ratio R may be a large number (i.e., a "low" gear ratio), e.g., R≥1,000 or even R≥5,000. Then the earlier precision in the wavelength tuning parameter x of $1/5^{th}$ of a degree becomes $1/25,000^{th}$ of a degree for R=5,000. This degree of resolution exceeds the previously stated example resolution requirement of $1/3,000^{th}$ of a degree.

In an example of tunable light source system 200, reference filter 310 is substantially the same as tunable filter 216, i.e., tunable filter bandwidth $\Delta\lambda_T = \Delta\lambda_R$. This allows for substantially the same signal processing in controller 150 for biosensor 102 measurements and reference measurements.

Optical Interrogation System Using the Tunable Light Source

The tunable light source 106 having a filter spectral linewidth matched to the biosensor resonance linewidth is suitable for use in swept-wavelength optical readers, including photodiode-based multichannel optical readers and CCD/CMOS-based imaging optical readers. The tunable light source 106 can replace the narrow-band tunable lasers used in prior art optical reader systems. The measured sensor spectrum is the convolution of the relatively wide spectral linewidth of incident beam 134I and the resonance linewidth of biosensor 102, and this operation automatically removes interference fringes from the sensor.

The simplicity and high performance of tunable light source 106 allows for compact imaging systems 114 and thus enables LID optical reader system 100 to be very compact, i.e., to have a small form factor, which in one example is 10 inches by 4 inches by 7 inches. This form factor allows system 100 to fit into a suitcase-sized or briefcase-sized housing, thus making the system easily transportable.

It will be apparent to those skilled in the art that various modifications to the preferred embodiment of the disclosure as described herein can be made without departing from the scope of the disclosure as defined in the appended claims. Thus, the disclosure covers the modifications and variations provided they come within the scope of the appended claims and the equivalents thereto.

What is claimed is:

1. A tunable light source system, comprising:
    a tunable light source that emits a tunable light beam having a tunable center wavelength $\lambda_C$;
    an angle-adjustable filter and an angle-adjustment unit operably connected to the angle-adjustable filter to adjust a filter angle to tune the tunable center wavelength $\lambda_C$ of the tunable light beam;
    a light-deflecting element disposed in the tunable light beam downstream of the angle-adjustable filter to deflect at least a portion of the tunable light beam that passes through the angle-adjustable filter;
    a reference filter having a reference bandwidth and a reference-filter function $SR_T(\lambda)$ that is substantially linear, the reference filter being disposed to filter the deflected portion of the tunable light beam to form a filtered light beam;
    a single photodetector arranged to detect the filtered light beam and generate a single detector electrical signal representative of a detected light spectrum; and
    a controller operably connected to the tunable light source and the single photodetector, the controller being configured to receive the single detector electrical signal and determine therefrom the tunable center wavelength $\lambda_C$ of the tunable light beam.

2. The system according to claim 1,
    further including an optical imager synchronized with the tunable light source and operably connected to the controller, the optical image arranged to capture a series of RWG biosensor images each of which corresponds to a distinct center wavelength $\lambda_C$ of the tunable light beam.

3. The system of claim 1, further comprising the controller having instructions embodied in a non-transitory computer-readable medium that cause the controller to calculate the center wavelength.

4. The system of claim 1, wherein the controller is operably connected to the angle-adjustable filter to adjust a filter angle to tune the tunable center wavelength $\lambda_C$ of the tunable light beam.

5. The system according to claim 4, wherein the angle-adjustment unit further comprises:
   a gear box having a gear ratio and mechanically connected to the tunable filter;
   a motor mechanically connected to the gear box; and
   a motor controller operably connected to the motor.

6. The system of claim 4, wherein the angle-adjustment unit further comprises:
   a motor mechanically connected to the tunable filter; and
   a motor controller operably connected to the motor.

7. The system of claim 1, wherein the tunable light source includes a broadband light source having one of a superluminescent diode (SLD) and a light-emitting diode (LED).

8. A label-independent optical reader for reading at least one resonant waveguide grating (RWG) biosensor supported by a microplate, comprising:
   the tunable light source system of claim 1 that emits the tunable light beam over a range of center wavelengths $\lambda_C$;
   an illumination system configured to direct the tunable light beam to the at least one RWG biosensor and form a corresponding reflected light beam; and
   an optical imager arranged to receive the reflected light beam and configured to form therefrom a series of digital images each of which corresponds to a different determined tunable center wavelength $\lambda_C$.

9. The label-independent optical reader of claim 8, further comprising a controller configured to receive and process the digital images to establish the occurrence of biochemical reaction in the at least one RWG biosensor.

10. A method of measuring a center wavelength $\lambda_C$ of a tunable light beam from a tunable light source, comprising:
   a) filtering a portion of a tunable light beam while tuning the center wavelength $\lambda_C$ by passing a broadband light beam through an angle-adjustable filter and adjusting an angle of the angle-adjustable filter to form a first light beam;
   b) passing the first light beam through a reference filter to form a reference-filtered tunable light beam, wherein the reference filter has reference-filter function $SR_T(\lambda)$ that is substantially linear between a lower wavelength $\lambda_L$ and an upper wavelength $\lambda_U$;
   c) detecting with a single photodetector a portion of the reference-filtered tunable light beam and generating therefrom a single detector signal $SD(\lambda_C)$ that varies with the center wavelength $\lambda_C$; and
   d) determining the center wavelength $\lambda_C$ based only on the single detector signal $SD(\lambda_C)$.

11. The method according to claim 10, wherein further comprising:
   capturing a series of RWG biosensor images each having a different center wavelength; and
   for each captured RWG biosensor image, performing acts a) through d) to determine a corresponding one of the different determined center wavelengths $\lambda_C$.

12. The method of claim 10, further comprising:
   using a portion of the tunable light beam to measure a RWG biosensor substantially simultaneously with detecting the reference-filtered tunable light beam; and
   assigning the determined center wavelength $\lambda_C$ to the RWG biosensor measurement.

13. The method according to claim 10, wherein the angle-adjustable filter has a spectral band-pass $\Delta\lambda_T$, further comprising performing the reference filtering with a reference filter having a reference band-pass $\Delta\lambda_R$ that is substantially the same as the angle-adjustable filter spectral band-pass $\Delta\lambda_T$.

14. A tunable light source system that emits a wavelength-tunable light beam and measures a center wavelength $\lambda_C$ of the wavelength-tunable light beam, comprising:
   an angle-adjustable filter and an angle-adjustment unit operably connected to the angle-adjustable filter to adjust a filter angle to tune the tunable center wavelength $\lambda_C$ of the wavelength-tunable light beam;
   a light-deflecting element disposed downstream of the angle-adjustable filter and arranged to deflect at least a portion of the wavelength-tunable light beam;
   a reference filter having a linearly varying reference bandwidth and that filters the deflected portion of the wavelength-tunable light beam to form a filtered light beam;
   a single photodetector that detects the filtered light beam and generates a single detector electrical signal representative of a detected light spectrum; and
   a controller operably connected to the tunable light source and the single photodetector and configured to receive the single detector electrical signal and determine therefrom the center wavelength.

15. The tunable light source system according to claim 14, further comprising:
   a tunable light source that emits the wavelength-tunable light beam;
   an optical imager synchronized with the tunable light source and operably connected to the controller, the optical image arranged to capture a series of RWG biosensor images each of which corresponds to a distinct determined center wavelength $\lambda_C$ of the tunable light beam.

16. The tunable light source system of claim 14, wherein the single photodetector detects a reflected portion of the filtered light beam.

* * * * *